US012788752B2

(12) United States Patent
Kim et al.

(10) Patent No.: US 12,788,752 B2
(45) Date of Patent: Nov. 10, 2026

(54) PHARMACEUTICAL COMPOSITION FOR PREVENTING OR TREATING TUMOR, AND USE THEREOF

(71) Applicant: TIUMBIO CO., LTD., Seongnam-si (KR)

(72) Inventors: Hun-Taek Kim, Seongnam-si (KR); Jeongmin Seo, Seongnam-si (KR); Nam-Hoon Kim, Seongnam-si (KR); Seung-Hyun Kim, Seongnam-si (KR); Jihyun Lee, Seongnam-si (KR); Ji Hyun Noh, Seongnam-si (KR); Chanhee Yu, Seongnam-si (KR)

(73) Assignee: TIUMBIO CO., LTD., Seongnam-si (KR)

( * ) Notice: Subject to any disclaimer, the term of this patent is extended or adjusted under 35 U.S.C. 154(b) by 346 days.

(21) Appl. No.: 18/292,228

(22) PCT Filed: Jul. 28, 2022

(86) PCT No.: PCT/KR2022/011149
§ 371 (c)(1),
(2) Date: Jan. 25, 2024

(87) PCT Pub. No.: WO2023/008936
PCT Pub. Date: Feb. 2, 2023

(65) Prior Publication Data

US 2024/0342166 A1 Oct. 17, 2024

(30) Foreign Application Priority Data

Jul. 28, 2021 (KR) ........................ 10-2021-0099500

(51) Int. Cl.
*A61K 31/498* (2006.01)
*A61K 39/00* (2006.01)
*A61K 45/06* (2006.01)
*A61P 35/00* (2006.01)
*C07K 16/28* (2006.01)

(52) U.S. Cl.
CPC ............ *A61K 31/498* (2013.01); *A61K 45/06* (2013.01); *A61P 35/00* (2018.01); *C07K 16/2818* (2013.01); *A61K 2039/505* (2013.01)

(58) Field of Classification Search
CPC .............. C07K 16/2818; A61K 31/498; A61K 45/06; A61P 35/00
See application file for complete search history.

(56) References Cited

U.S. PATENT DOCUMENTS

| | | | |
|---|---|---|---|
| 10,632,110 | B2 | 4/2020 | Ha et al. |
| 11,440,963 | B2 | 9/2022 | Strauss et al. |

FOREIGN PATENT DOCUMENTS

| | | | |
|---|---|---|---|
| KR | 10-2017-0122799 | A | 11/2017 |
| KR | 10-2017-0123593 | A | 11/2017 |
| KR | 10-2220275 | B1 | 2/2021 |
| WO | 2011/056494 | A1 | 5/2011 |
| WO | 2013/009140 | A2 | 1/2013 |
| WO | 2015/119930 | A1 | 8/2015 |
| WO | 2017/087589 | A2 | 5/2017 |
| WO | 2019/090263 | A1 | 5/2019 |
| WO | 2019/099838 | A1 | 5/2019 |
| WO | 2021/142448 | A2 | 7/2021 |

OTHER PUBLICATIONS

International Search Report for PCT/KR2022/011149 dated Nov. 3, 2022 (PCT/ISA/210).
Rikke B. Holmgaard, et al., "Targeting the TGFβ pathway with galunisertib, a TGFβRI small molecule inhibitor, promotes anti-tumor immunity leading to durable, complete responses, as monotherapy and in combination with checkpoint blockade," Journal for ImmunoTherapy of Cancer, 2018, vol. 6, No. 47, pp. 1-15 (15 pages total).
Ernest Nadal, et al., "A phase Ib/II study of galunisertib in combination with nivolumab in solid tumors and non-small cell lung cancer," BMC Cancer, 2023, vol. 23, No. 708, pp. 1-13 (13 pages total).
Alessandra Castiglioni, et al., "Combined PD-L1/TGFβ blockade allows expansion and differentiation of stem cell-like CD8 T cells in immune excluded tumors," Nature Communications, Aug. 5, 2023, vol. 14, No. 4703, pp. 1-19 (19 pages total).
Linwei Li, et al., "Therapeutic targeting of VEGF and/or TGF-β to enhance anti-PD-(L)1 therapy: The evidence from clinical trials," Frontiers in Oncology, Jul. 26, 2022, pp. 1-13 (13 pages total).
Tianye Li, et al., "Bispecific antibody targeting TGF-β and PD-L1 for synergistic cancer immunotherapy," Frontiers in Immunology, Jul. 13, 2023, pp. 1-14 (14 pages total).
Melissa T. Bu, et al., "The roles of TGF-β and VEGF pathways in the suppression of antitumor immunity in melanoma and other solid tumors," Pharmacology & Therapeutics 240, May 14, 2022, pp. 1-14 (14 pages total).
Tae Won Kim, et al., "Efficacy and Safety of Vactosertib and Pembrolizumab Combination in Patients with Previously Treated Microsatellite Stable Metastatic Colorectal Cancer," MEdPACTO, ESMO 2023, Annual Meeting, Oct. 20-24, 2023, #618P (1 page total).
Mengke Niu, et al., "Synergistic efficacy of simultaneous anti-TGF-β/VEGF bispecific antibody and PD-1 blockade in cancer therapy," Journal of Hematology & Oncology, 2023, vol. 16, No. 94, pp. 1-23 (23 pages total).

(Continued)

*Primary Examiner* — Kamal A Saeed
(74) *Attorney, Agent, or Firm* — Sughrue Mion, PLLC

(57) ABSTRACT

According to an aspect of the technology disclosed by the present application, the present invention relates to a pharmaceutical composition for preventing or treating a tumor, including a low-molecular kinase inhibitor which blocks the signaling pathway of transforming growth factor-β (TGF-β), in which, by administration of the low-molecular kinase that blocks the TGF-β signaling pathway, in combination with at least one of an immune checkpoint regulator and a receptor tyrosine kinase inhibitor, a tumor therapeutic or tumor growth inhibitory effect is excellent in a patient who needs tumor therapy or tumor growth inhibition, compared to when the low-molecular kinase inhibitor, immune checkpoint regulator, or receptor tyrosine kinase inhibitor is administered alone.

6 Claims, 18 Drawing Sheets

(56) References Cited

OTHER PUBLICATIONS

James L. Gulley, et al., "Dual inhibition of TGF-β and PD-L1: a novel approach to cancer treatment," Molecular Oncology, 2022, pp. 2117-2134 (1-18 pages total).
Ming Yi, et al., "TGF-β: A novel predictor and target for anti-PD-1/PD-L1 therapy," Frontiers in Immunology, Dec. 19, 2022, pp. 1-12 (12 pages total).
Fabrice Barlesi, et al., "Bintrafusp Alfa, a Bifunctional Fusion Protein Targeting TGF-β and PD-L1, in Patients with Non-Small Cell Lung Cancer Resistant or Refractory to Immune Checkpoint Inhibitors," The Oncologist, 2023, vol. 28, pp. 258-267 (10 pages total).
Yan Lan, et al., "Colocalized targeting of TGF-β and PD-L1 by bintrafusp alfa elicits distinct antitumor responses," Journal for ImmunoTherapy of Cancer, 2022, vol. 10, pp. 1-14 (14 pages total).
Won Suk Lee, et al., "Combination of anti-angiogenic therapy and immune checkpoint blockade normalizes vascularimmune crosstalk to potentiate cancer immunity," Experimental & Molecular Medicine, 2020, vol. 52, pp. 1475-1485 (11 pages total).
Yuxiao Song, et al. "Anti-angiogenic Agents in Combination With Immune Checkpoint Inhibitors: A Promising Strategy for Cancer Treatment," Frontiers in Immunology, Aug. 25, 2020, vol. 11, Article 1956, pp. 1-17 (17 pages total).
Yu Kato, et al., "Lenvatinib plus anti-PD-1 antibody combination treatment activates CD8+ T cells through reduction of tumor-associated macrophage and activation of the interferon pathway," PLOS ONE, Feb. 27, 2019, pp. 1-18 (18 pages total).
Samuel J. Klempner, et al., "Ramucirumab plus pembrolizumab: can we make the maths work?," Lancet Oncology, Jul. 10, 2019, pp. 1-3 (3 pages total).
Mark J. Selby, et al., "Preclinical Development of Ipilimumab and Nivolumab Combination Immunotherapy: Mouse Tumor Models, In Vitro Functional Studies, and Cynomolgus Macaque Toxicology," PLOS ONE, Sep. 9, 2016, pp. 1-19 (19 pages total).
Jedd D. Wolchok, et al., "Safety and clinical activity of combined PD-1 (nivolumab) and CTLA-4 (ipilimumab) blockade in advanced melanoma patients," N. Engl. J. Med., Jul. 11, 2013, vol. 369, No. 2, pp. 122-133 (19 pages total).
T. Yoshino et al., "Pembrolizumab plus lenvatinib versus standard of care for previously treated metastatic colorectal cancer (mCRC): Phase III LEAP-017 study," Annals of Oncology, Abstracts, vol. 32, Issue S5, 2021, S580 (1 page total).
Marwan Fakih, et al., "Regorafenib plus nivolumab in patients with mismatch repair-proficient/microsatellite stable metastatic colorectal cancer: a single-arm, open-label, multicentre phase 2 study," Articles, 2023, vol. 58, pp. 1-15 (15 pages total).
Extended European Search Report dated Jul. 7, 2025, issued in European application No. 22849912.5.
Siwen Hu-Lieskovan et al., "Addressing resistance to immune checkpoint inhibitor therapy: an urgent unmet need", Future Oncology, Jan. 21, 2021, vol. 17, No. 11, pp. 1401-1439.
Heng Sheng Sow et al., "Combined Inhibition of TGF-β Signaling and the PD-L1 Immune Checkpoint is Differentially Effective in Tumor Models", Cells, Apr. 5, 2019, vol. 8, No. 320 (14 pages).
Sandrine Faivre et al., "Molecular therapies for HCC: Looking outside the box", Journal of Hepatology, 2020, vol. 72, pp. 342-352.
Davide Melisi et al., "Safety and activity of the TGFβ receptor I kinase inhibitor galunisertib plus the anti-PD-L1 antibody durvalumab in metastatic pancreatic cancer", Journal for Immuno Therapy of Cancer, Mar. 9, 2021, vol. 9, pp. 1-10.
Yuji Yamamoto et al., "Lenvatinib, an angiogenesis inhibitor targeting VEGFR/FGFR, shows broad antitumor activity in human tumor xenograft models associated with microvessel density and pericyte coverage", Vascular Cell, 2014, vol. 6, No. 18, pp. 1-13.

[Figure 1]
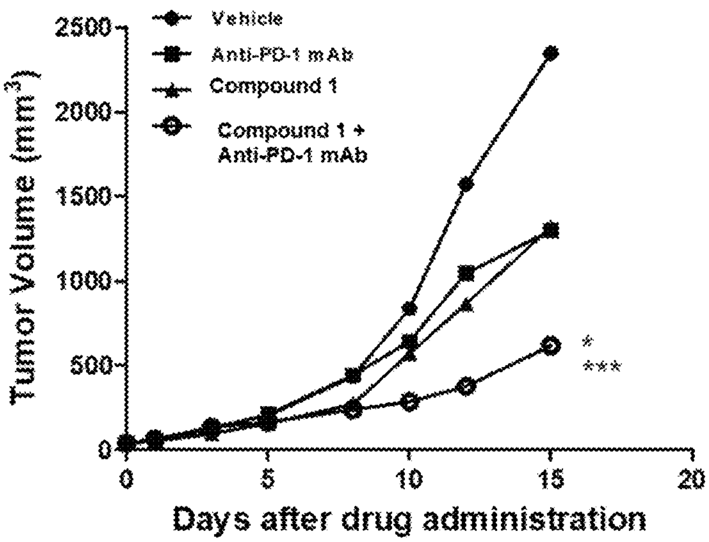
*:P<0.05 Two-way ANOVA vs. anti-PD-1
***:P<0.001 Two-way ANOVA vs. Compound 1
[Figure 2]
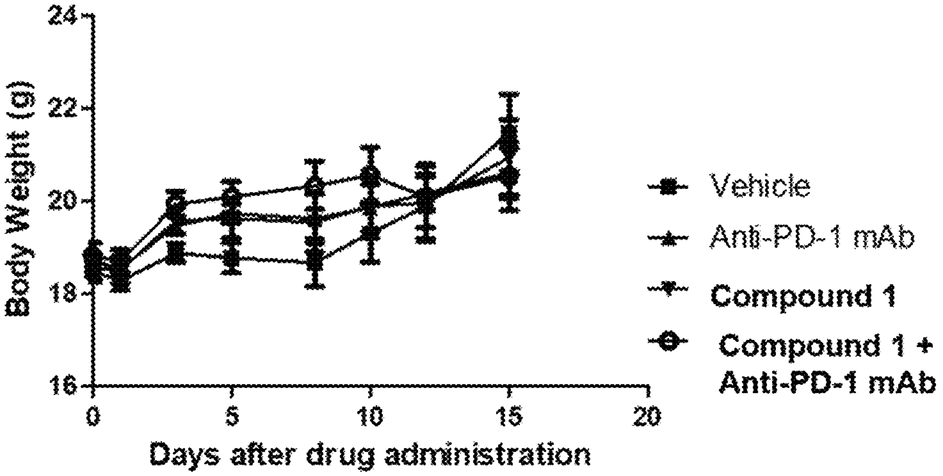

[Figure 3]
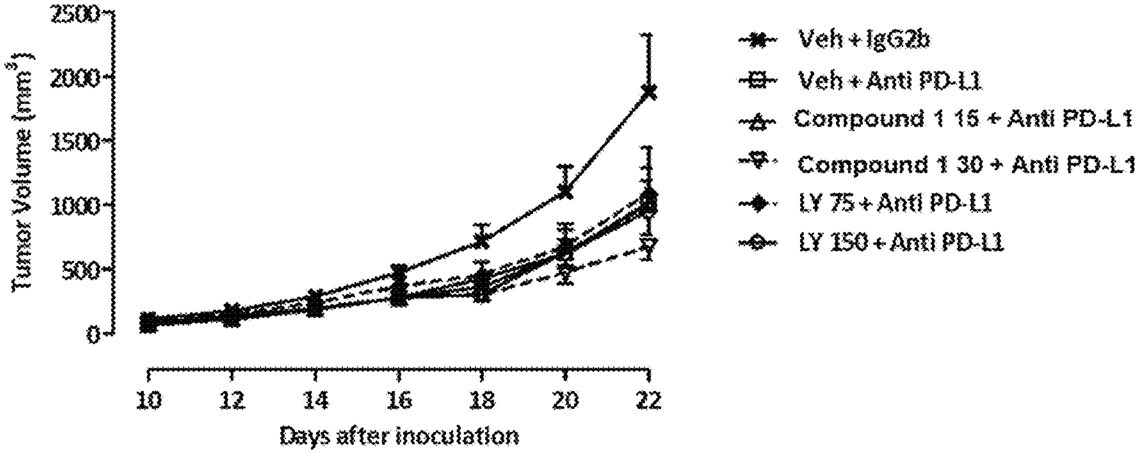
| *versus Veh+IgG2b* | d10 | d12 | d14 | d16 | d18 | d20 | d22 |
|---|---|---|---|---|---|---|---|
| Veh + α-PD-L1 | *** | *** | ** | * | * | * | |
| Compound 1 15 + α PD-L1 | *** | ** | * | * | ** | | |
| Compound 1 30 + α PD-L1 | *** | ** | ** | ** | ** | ** | * |
| LY 75 + α-PD-L1 | | | | | | | |
| LY 150 + α-PD-L1 | ** | * | ** | * | * | | |

[Figure 4]
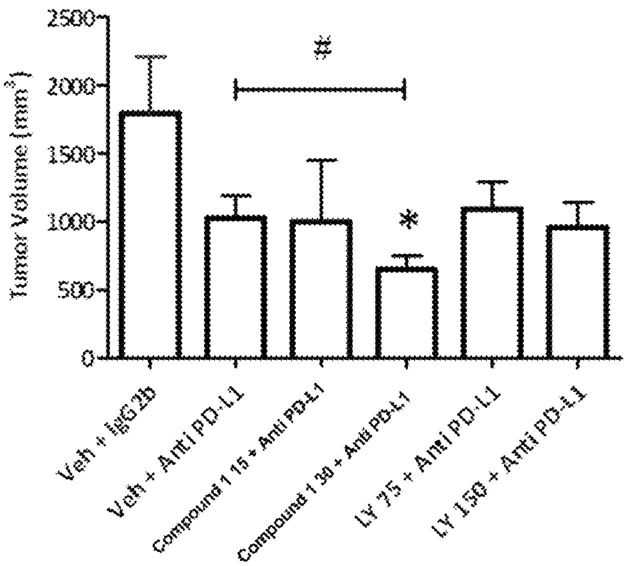
[Figure 5]
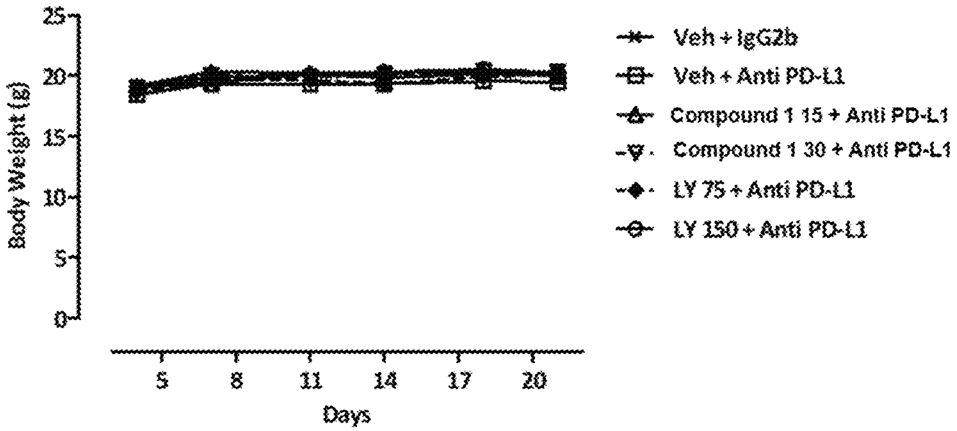

[Figure 6A]
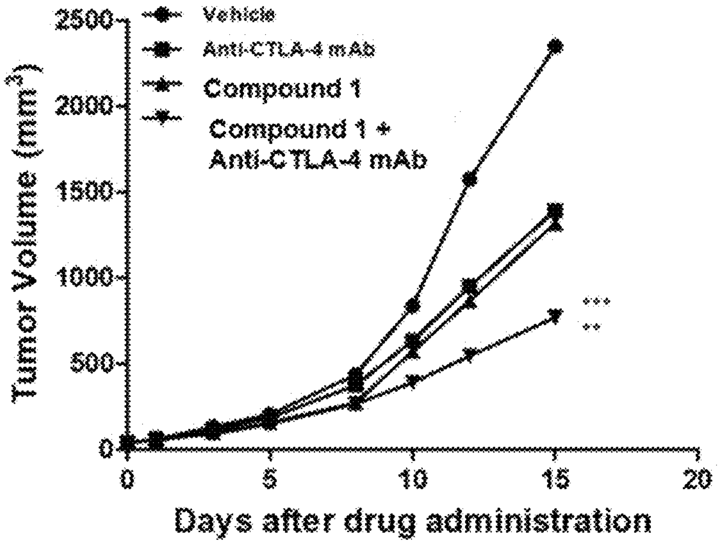
***: P<0.001 Two-way ANOVA vs. anti-CTLA4 alone
**: P<0.01 Two-way ANOVA vs. Compound 1 alone
[Figure 6B]
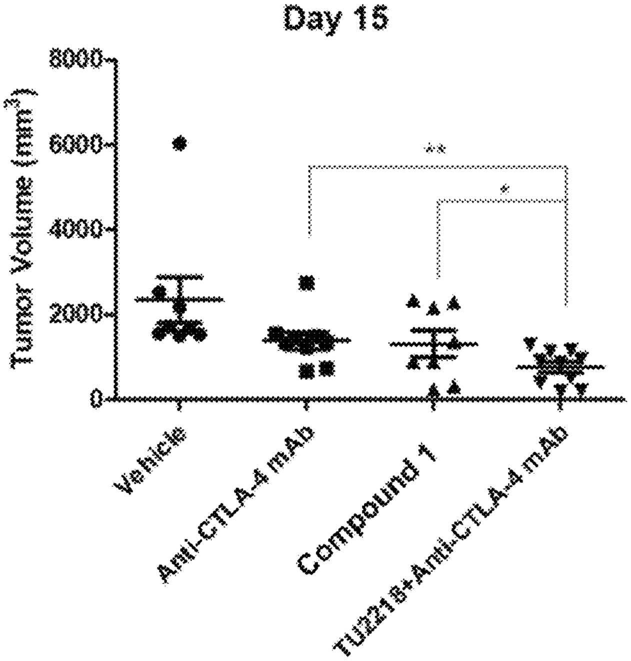
**: P<0.01 one-tailed t-test vs. anti-CTLA4 alone
*: P<0.01 one-tailed t-test vs. Compound 1 alone

[Figure 7]
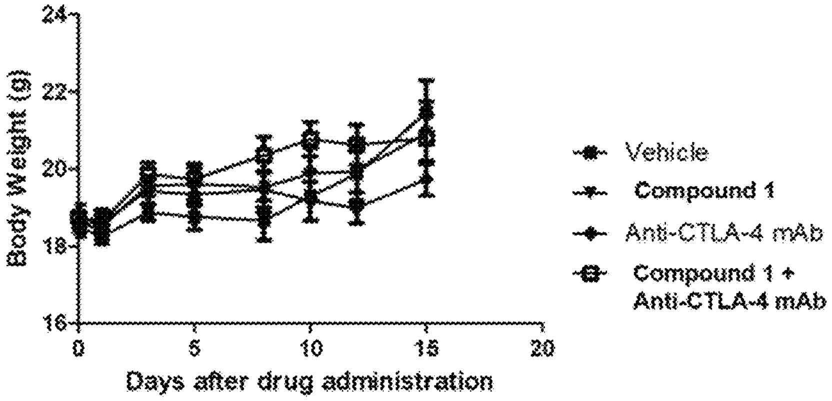

[Figure 8A]
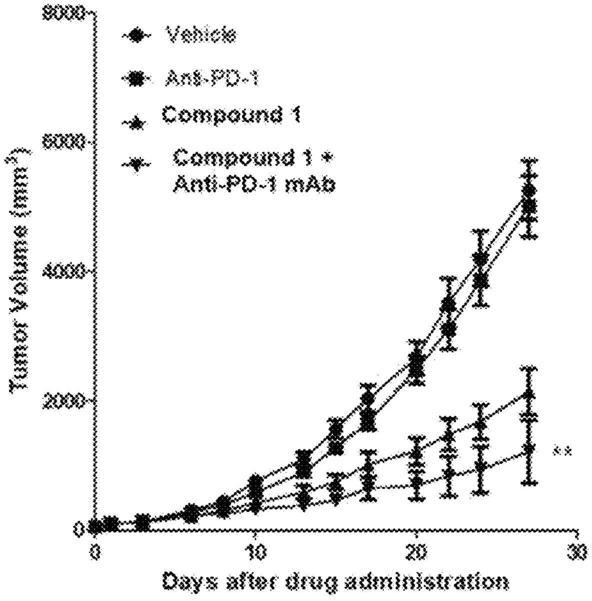
**: P<0.01 Two-way ANOVA, Bonferroni test vs. Compound 1(day 26)
[Figure 8B]
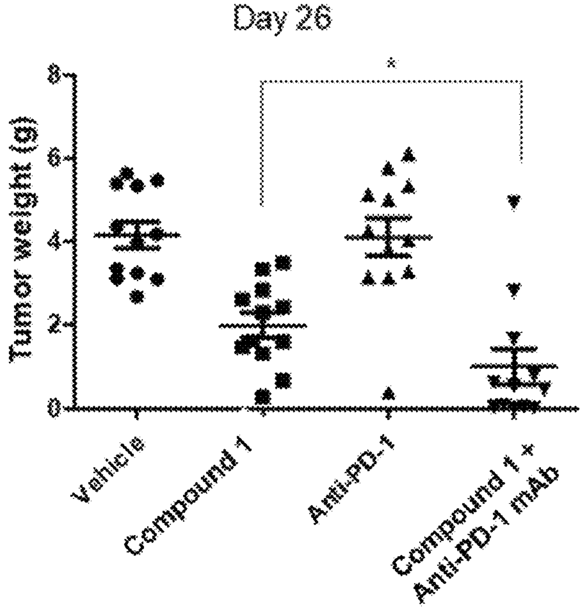
*: P<0.05 one-tailed t-test

[Figure 9A]
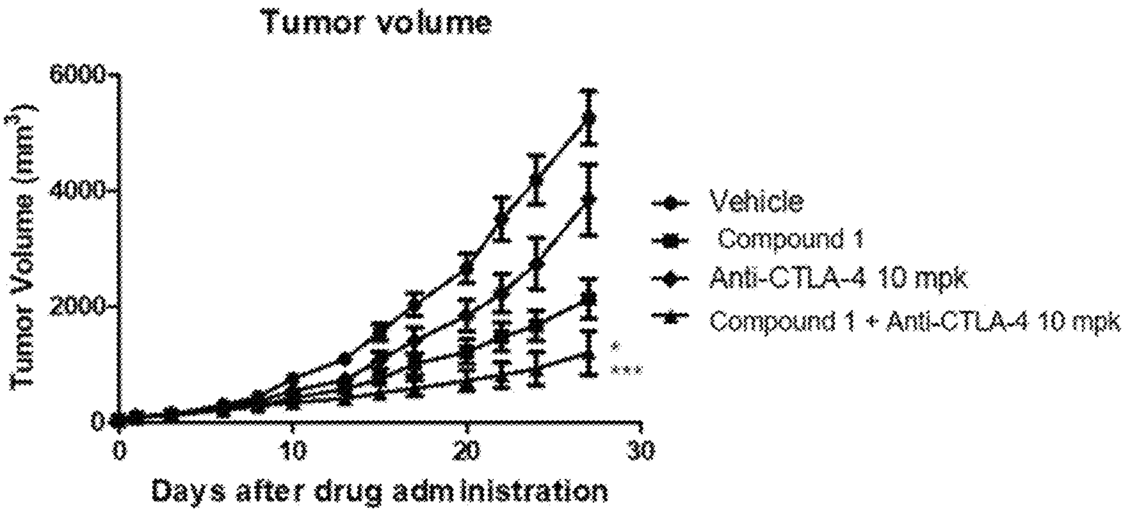
*: P<0.05 Two-way ANOVA vs. Compound 1
***: P<0.001 Two-way ANOVA vs. vehicle
[Figure 9B]
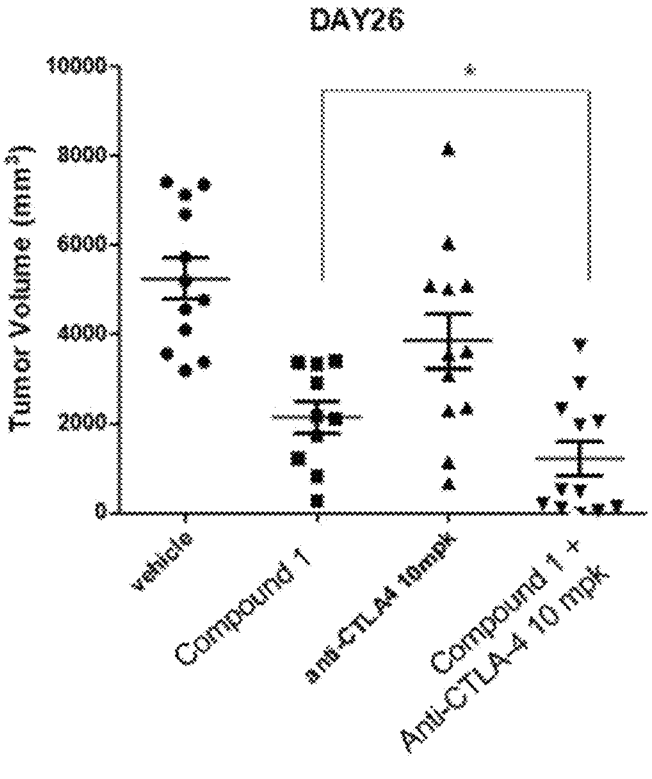
*: P<0.05 one-tailed t-test

[Figure 10]
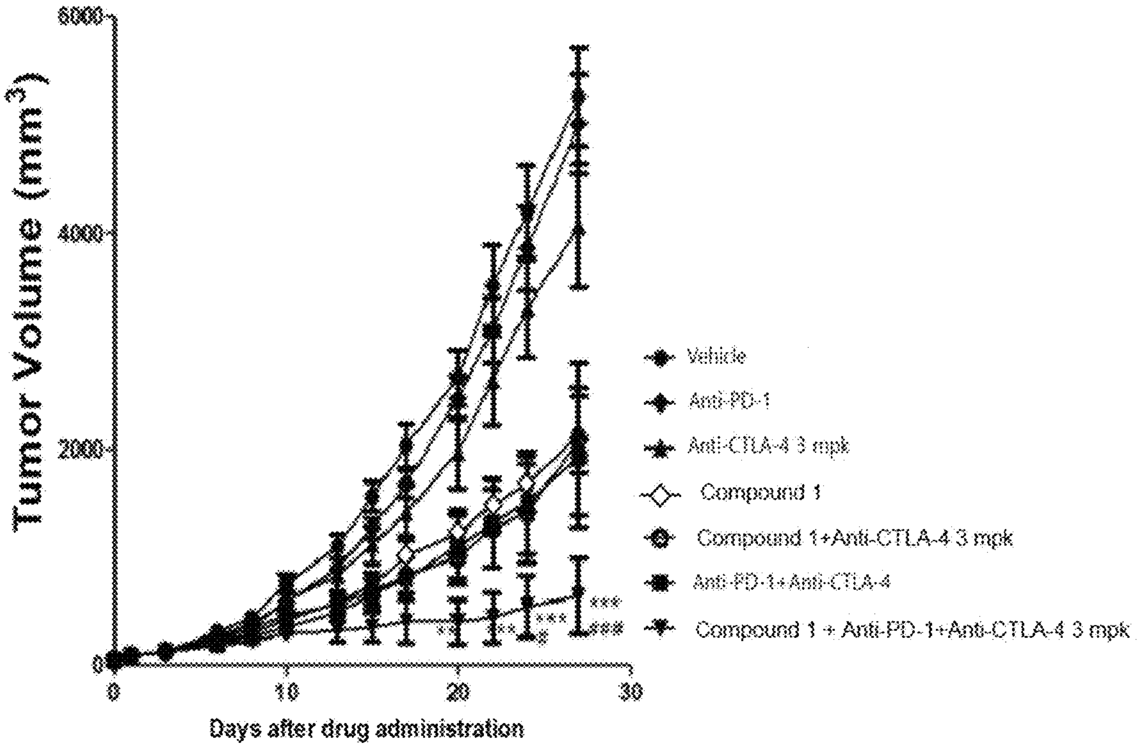
: P<0.01, *: P<0.001 Two-way ANOVA, Bonferroni test vs. Compound 1
#: P<0.05, ###: P<0.001 Two-way ANOVA, Bonferroni test vs. anti-PD1+ anti-CTLA4

[Figure 11]
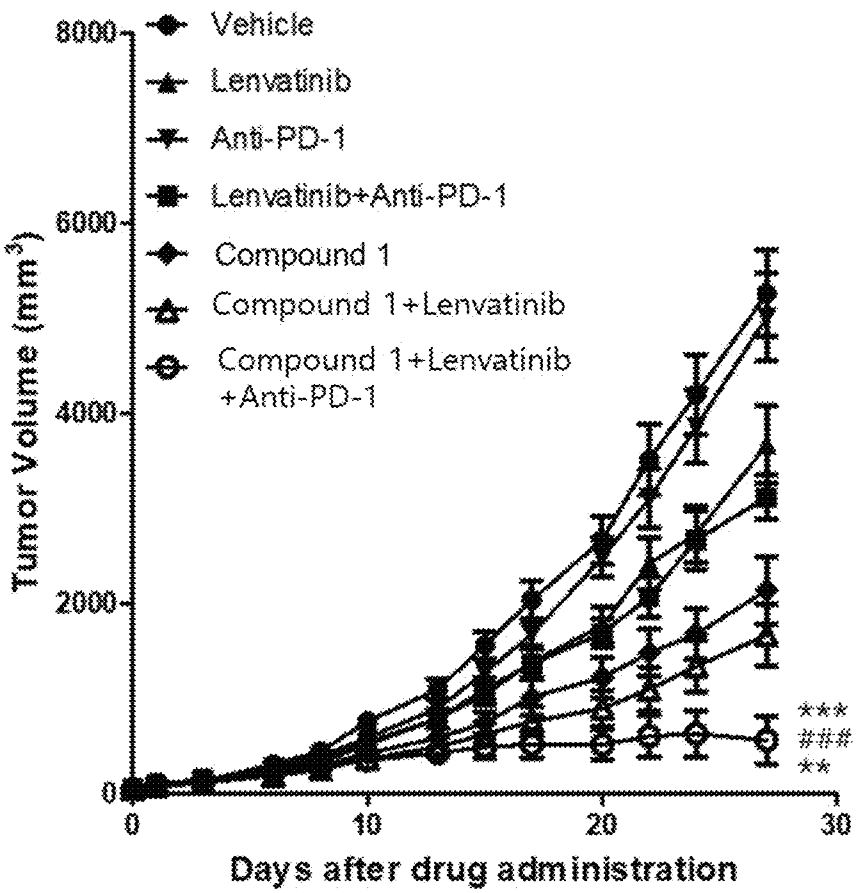
***: P<0.001 Two-way ANOVA vs. Compound 1
: P<0.001 Two-way ANOVA vs. Compound 1+Lenvatinib
**: P<0.01 Two-way ANOVA vs. anti-PD1+Lenvatinib

[Figure 12]
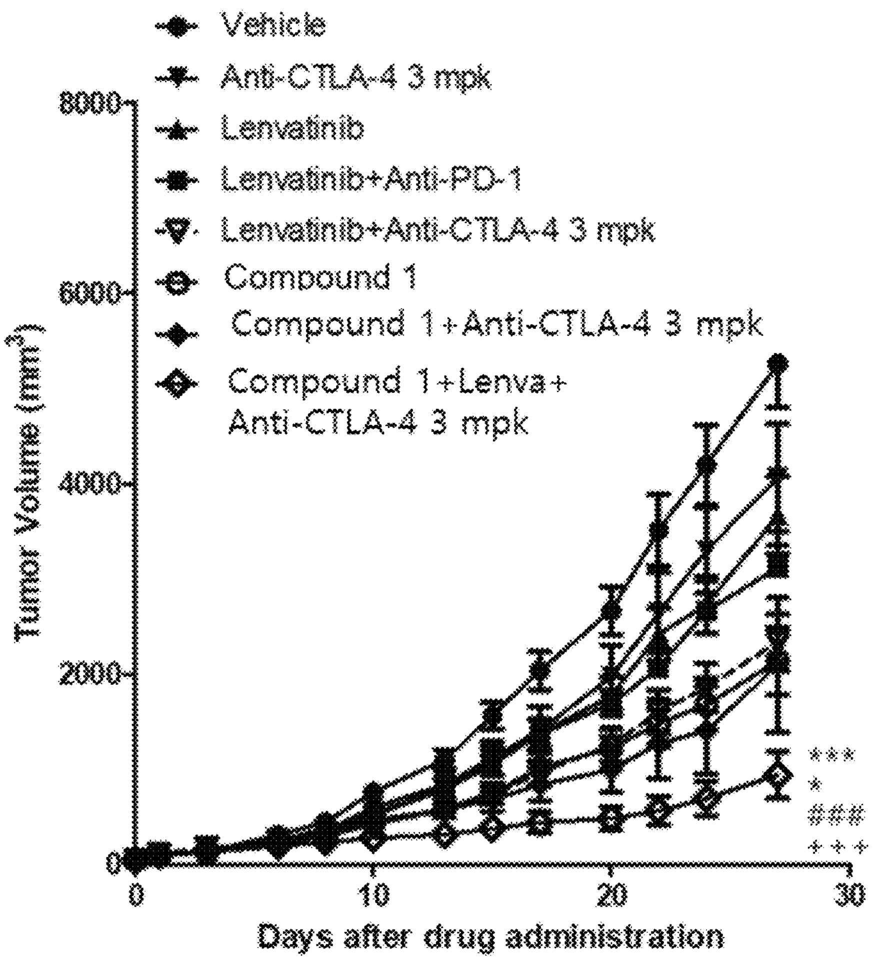
***: P<0.001 Two-way ANOVA vs. Lenvatinib+anti-CTLA4
*: P<0.05 Two-way ANOVA vs. Compound 1+anti-CTLA4
: P<0.001 Two-way ANOVA vs. Compound 1
+++: P<0.001 Two-way ANOVA vs. anti-PD1+Lenvatinib

[Figure 13]
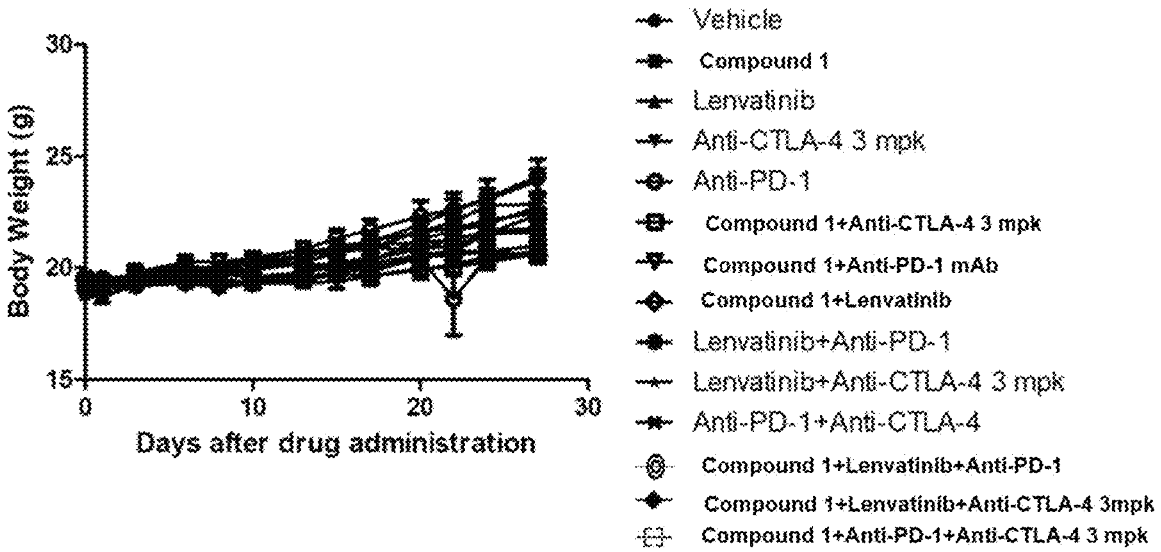

[Figure 14]
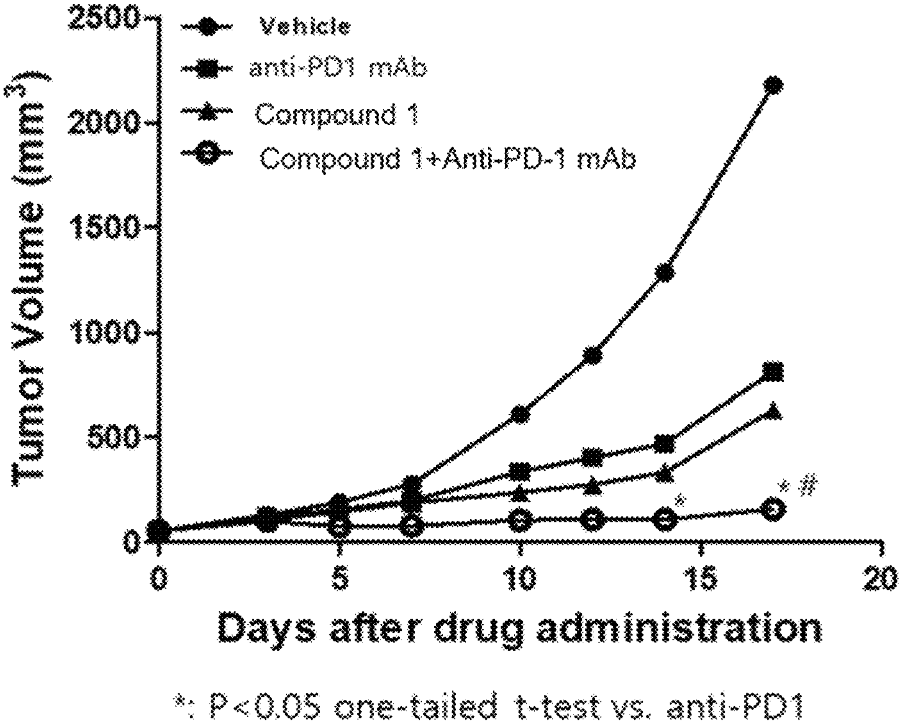
*: P<0.05 one-tailed t-test vs. anti-PD1
#: P<0.05 one-tailed t-test vs. Compound 1

[Figure 15]
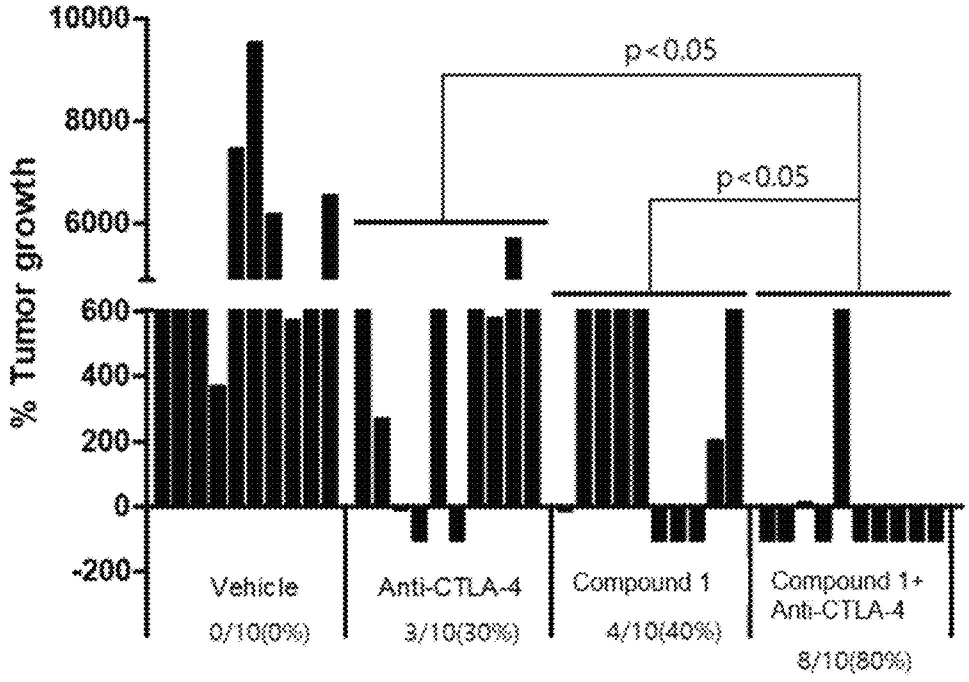
One-way ANOVA, Tukey's multiple comparison test, frequency of CR
[Figure 16]
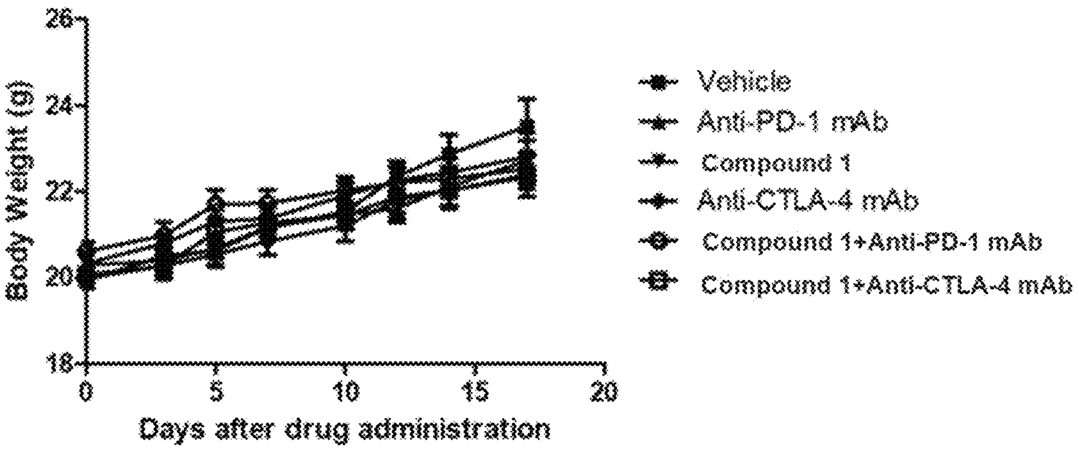

[Figure 17A]
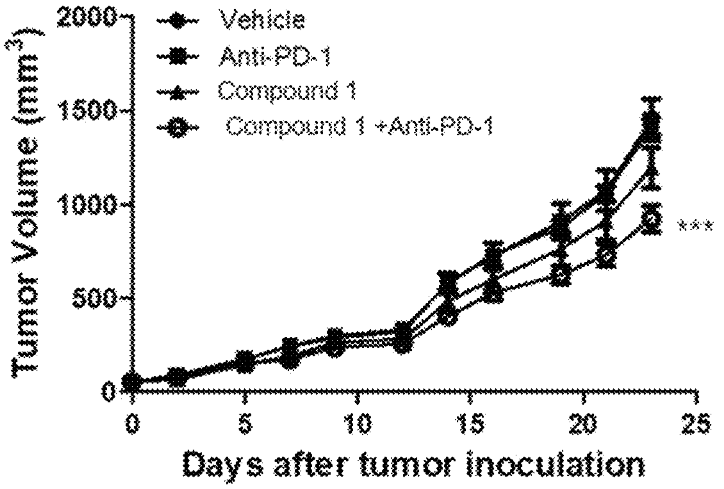
***: P<0.001 Two-way ANOVA vs. vehicle
[Figure 17B]
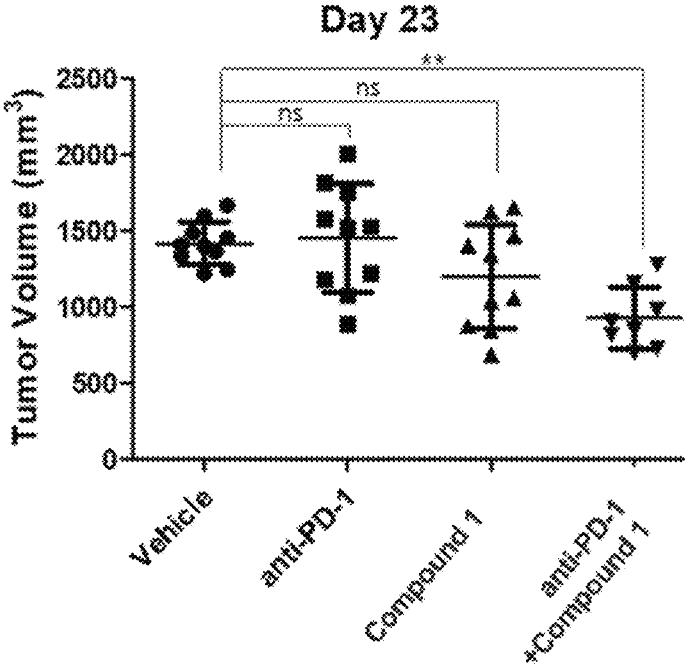

[Figure 18A]
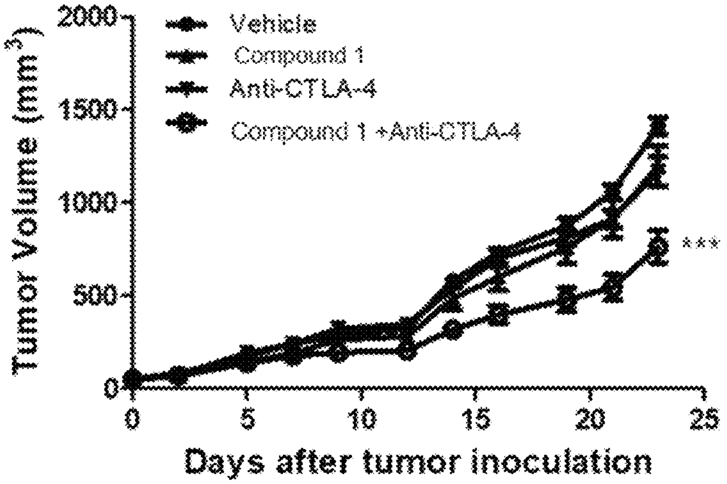
***: P<0.001 Two-way ANOVA vs. vehicle
[Figure 18B]
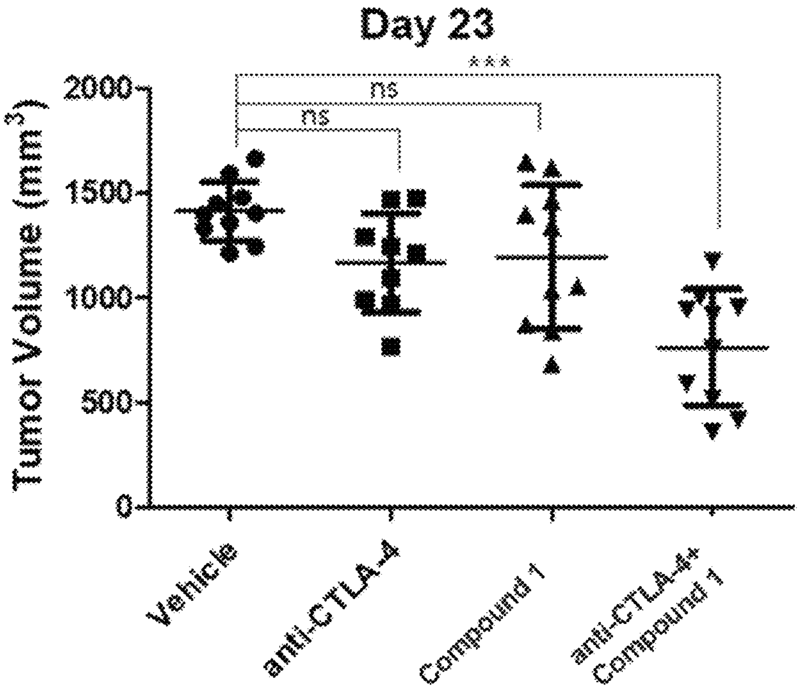
***: P<0.001 one-way ANOVA, Tukey's test vs. vehicle

[Figure 19]
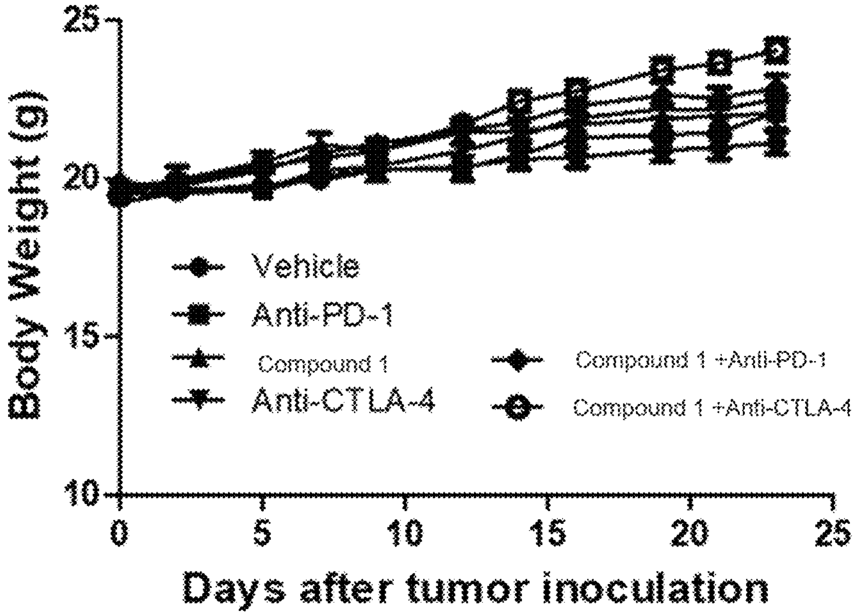

[Figure 20A]
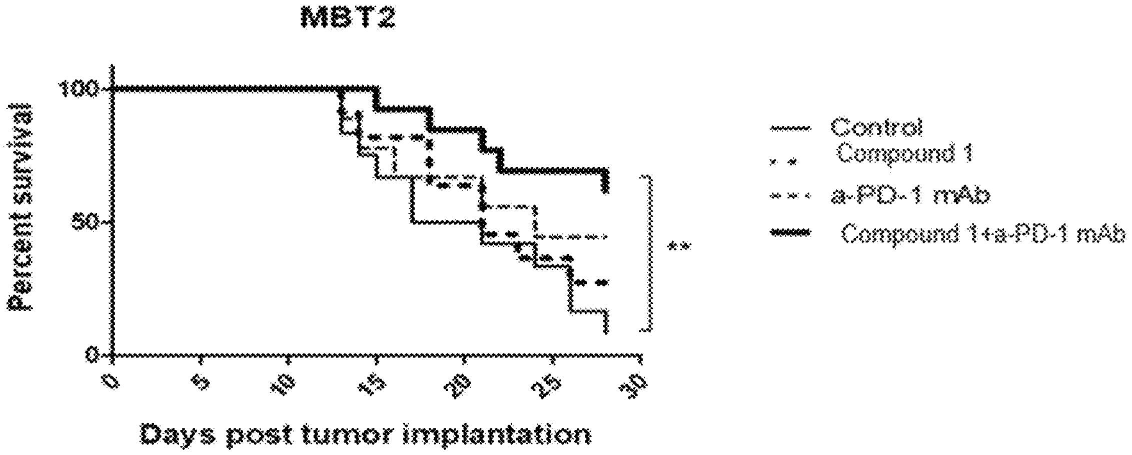
| Log-rank (Mantel-Cox) Test | |
|---|---|
| Chi square | 8.195 |
| df | 1 |
| P value | 0.0042 |
| P value summary | ** |
| Are the survival curves sig different? | Yes |

[Figure 20B]
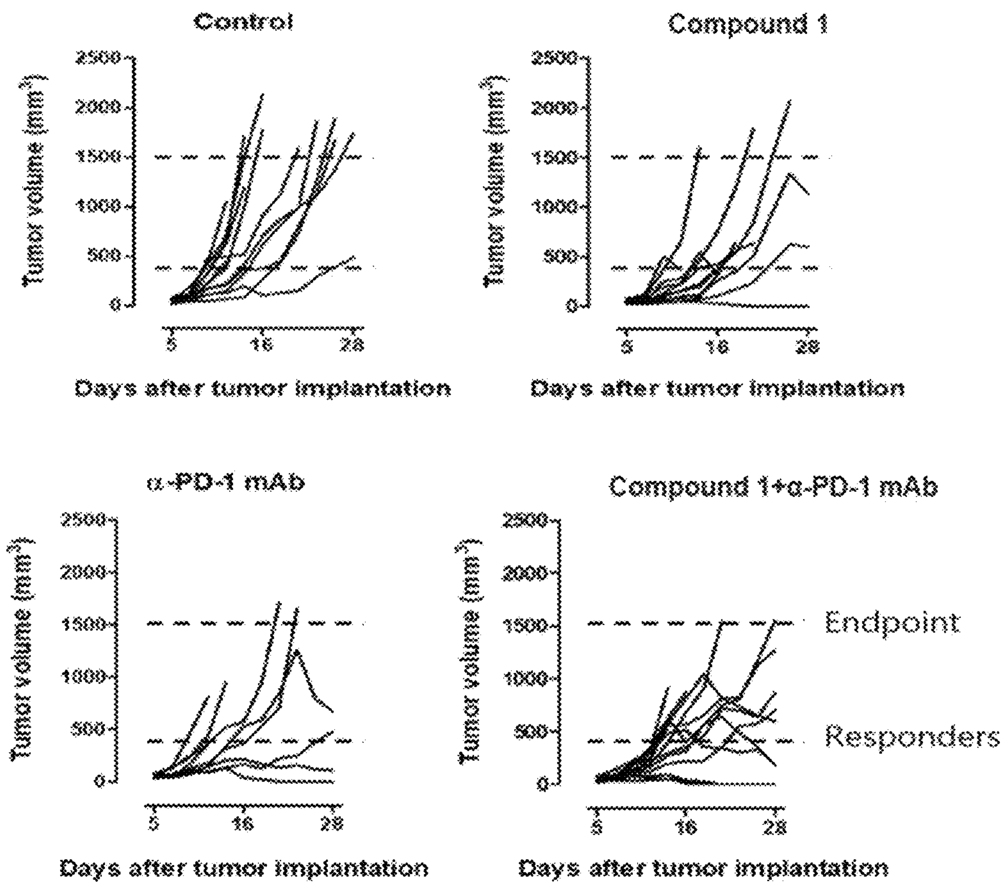
[Figure 21]
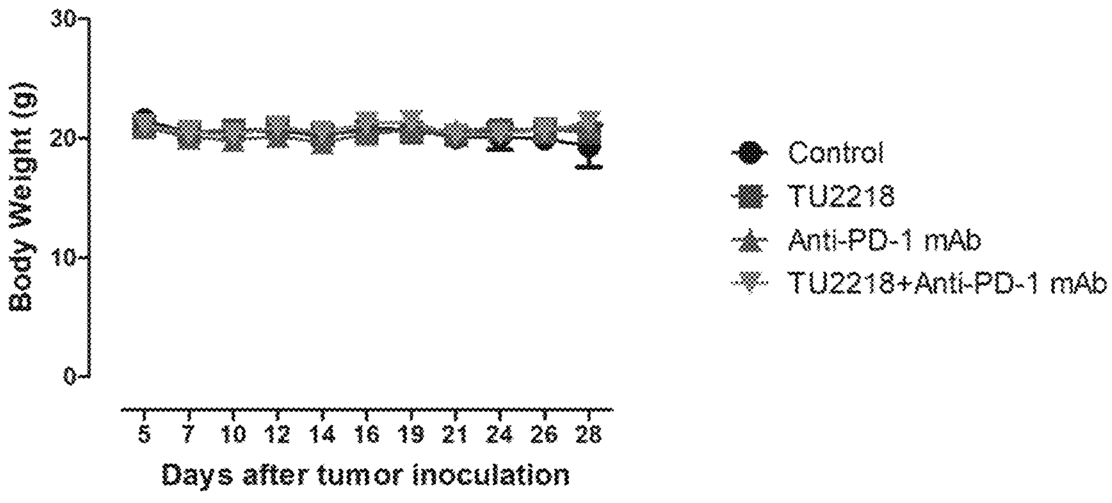

PHARMACEUTICAL COMPOSITION FOR PREVENTING OR TREATING TUMOR, AND USE THEREOF

CROSS REFERENCE TO RELATED APPLICATIONS

This application is a National Stage of International Application No. PCT/KR2022/011149 filed Jul. 28, 2022, claiming priority based on Korean Patent Application No. 10-2021-0099500 filed Jul. 28, 2021.

TECHNICAL FIELD

The present invention relates to a pharmaceutical composition for preventing or treating a tumor, a method for preventing or treating a tumor, and a use of the pharmaceutical composition, in which a low-molecular kinase inhibitor that blocks the signaling pathway of transforming growth factor-β (TGF-β) is administered in combination with at least one among an immune checkpoint regulator and a receptor tyrosine kinase inhibitor.

BACKGROUND ART

Tumor cells are characterized in that the tumor cells secrete substances that make T cells inactive, thereby avoiding the attack of immune cells, changing the tumor microenvironment, rapidly dividing, as well as allowing the tumor cells to escape from the tissues in which they were generated and to spread to other tissues. Meanwhile, tumor cells create blood vessels on their own to obtain nutrients required for rapid growth and metastasis (Tumor angiogenesis).

Regulatory T cells are known to be main cells involved in immune avoidance of tumor cells, and several treatment strategies have been developed to reduce the number of regulatory T cells in tumor tissue. For example, as a method for reducing the number of T cells, chemotherapeutics for controlling an immunosuppressive response by administering cyclophosphamide (CP) at a low concentration, methods for using an immune checkpoint regulator such as an antibody targeting a molecule such as CD25, CTLA-4, or PD-1, or a chemokine receptor, which are specifically expressed by regulatory T cells, have been developed, and ipilimumab (YERVOY®) targeting CTLA-4 and pembrolizumab (Keytruda®) and nivolumab (OPDIVO™) targeting programmed cell death protein-1 (PD-1) have been approved by the U.S. Food and Drug Administration (FDA) for sale.

Meanwhile, vascular endothelial cell growth factor receptors (VEGFRs) 1 to 3, platelet-derived growth factor receptors (PDGFRs-α), rearranged during transfection (RET) receptor, and fibroblast growth factor receptors (FGFRs) 1 to 4 are receptor tyrosine kinases known to be involved in cell division and angiogenesis of tumor cells. Accordingly, drugs for selectively inhibiting receptor tyrosine kinase have been developed, and research on a method for increasing an anti-cancer treatment effect by using a combination of a receptor tyrosine kinase selective inhibitor and an immune checkpoint regulator has also been actively conducted. In addition, in 2021, the FDA approved advanced kidney cancer therapy and advanced endometrial cancer therapy of a combination of lenvatinib (LENVIMA®), which is a receptor tyrosine kinase inhibitor, and pembrolizumab, which is an anti-PD-1 antibody.

However, there are tumor patients who do not respond to treatment using the immune checkpoint regulator and/or receptor tyrosine kinase inhibitor. Due to the low response rate at which the immune checkpoint regulator is effective only in about 20%-30% of cancer patients, the development of a combined therapeutic agent for increasing the response rate of the immune checkpoint regulator and maximizing the effect is actively being carried out. In addition, there is a limitation in that the quality of life of a tumor patient deteriorates due to adverse effects such as a decrease in the body weight of a subject even if a previously developed tumor therapeutic agent is used. Therefore, there is a need to develop a novel treatment that has an excellent effect of suppressing tumor growth while having few adverse effects.

PRIOR ART DOCUMENT (Patent Document 1) Korean Patent No. 2220275

DISCLOSURE OF THE INVENTION

Technical Problem

The present inventors have found that the administration of a low-molecular kinase inhibitor that blocks the signaling pathway of TGF-β to a subject in combination with at least one selected from among an immune checkpoint regulator and a receptor tyrosine kinase inhibitor has better effects of suppressing tumor growth and is safer than the administration of the low-molecular kinase inhibitor that blocks the signaling pathway of TGF-β, the receptor tyrosine kinase inhibitor, or the immune checkpoint regulator alone, thereby completing the present invention.

Solution to Problem

In an embodiment of the present invention, the present invention provides a pharmaceutical composition for preventing or treating a tumor, the pharmaceutical composition including a low-molecular kinase inhibitor that blocks the signaling pathway of TGF-β, in which the low molecular kinase inhibitor that blocks the signaling pathway of TGF-β is administered in combination with at least one among an immune checkpoint regulator and a receptor tyrosine kinase inhibitor.

In another embodiment of the present invention, there is provided a pharmaceutical composition for preventing or treating a tumor, the pharmaceutical composition including a low-molecular kinase inhibitor that blocks the signaling pathway of TGF-β, and at least one among an immune checkpoint regulator and a receptor tyrosine kinase inhibitor.

In another embodiment of the present invention, the present invention provides a combination for preventing or treating a tumor, the combination including a low-molecular kinase inhibitor that blocks the signaling pathway of TGF-β, and at least one among an immune checkpoint regulator and a receptor tyrosine kinase inhibitor.

In another embodiment of the present invention, the present invention provides a method for preventing or treating a tumor in a subject, the method including administering to the subject a low-molecular kinase inhibitor that blocks the signaling pathway of TGF-β, and at least one among an immune checkpoint regulator and a receptor tyrosine kinase inhibitor.

In an embodiment of the present invention, the present invention provides a use of a low-molecular kinase inhibitor that blocks the signaling pathway of TGF-β, which is administered in combination with at least one among an immune checkpoint regulator and a receptor tyrosine kinase inhibitor for preparing a medicament for preventing or treating a tumor.

In an embodiment of the present invention, the present invention provides a kit for preventing or treating a tumor, the kit including a low-molecular kinase inhibitor that blocks the signaling pathway of TGF-β, and an instruction manual that instruct the administration of a low-molecular kinase inhibitor that blocks the signaling pathway of TGF-β in combination with at least one among an immune checkpoint regulator and a receptor tyrosine kinase inhibitor.

Advantageous Effects of Invention

The administration of a low-molecular kinase inhibitor that blocks the signaling pathway of TGF-β to a subject in combination with at least one selected from among an immune checkpoint regulator and a receptor tyrosine kinase inhibitor has superior effects of suppressing tumor growth to the use of the low-molecular kinase inhibitor, the immune checkpoint regulator, or the tyrosine kinase inhibitor alone.

BRIEF DESCRIPTION OF DRAWINGS

FIG. 1 shows the effect of suppressing a tumor volume increase in the co-administration of Compound 1 and anti-PD-1 antibody, a control group (vehicle), the administration of Compound 1 alone, and the administration of anti-PD-1 antibody alone in a melanoma mouse model.

FIG. 2 shows changes in the body weights of the control group (vehicle) and the study drug administration groups (Compound 1+anti-PD-1 antibody, Compound 1, and anti-PD-1 antibody) during a period of the study in the melanoma mouse model.

FIG. 3 shows the tumor volumes, by mean±SEM, of the control group (vehicle+anti-IgG2b antibody) and the study drug administration groups (vehicle+anti-PD-L1 antibody, Compound 1 (15 mg/kg/day)+anti-PD-L1 antibody, Compound 1 (30 mg/kg/day)+anti-PD-L1 antibody, LY2157299 (75 mg/kg/day)+anti-PD-L1 antibody, and LY2157299 (150 mg/kg/day)+anti-PD-L1 antibody) in the melanoma mouse model.

FIG. 4 shows the tumor volumes, on day 22 after the cell line inoculation, of the control group (vehicle+anti-IgG2b antibody) and the study drug administration groups (vehicle+anti-PD-L1 antibody, Compound 1 (15 mg/kg/day)+anti-PD-L1 antibody, Compound 1 (30 mg/kg/day)+anti-PD-L1 antibody, LY2157299 (75 mg/kg/day)+anti-PD-L1 antibody, and LY2157299 (150 mg/kg/day)+anti-PD-L1 antibody) in the melanoma mouse model.

FIG. 5 shows changes in the body weights, during a period of the study, of the control group (vehicle+anti-IgG2b antibody) and the study drug administration groups (vehicle+anti-PD-L1 antibody, Compound 1 (15 mg/kg/day)+anti-PD-L1 antibody, Compound 1 (30 mg/kg/day)+anti-PD-L1 antibody, LY2157299 (75 mg/kg/day)+anti-PD-L1 antibody, and LY2157299 (150 mg/kg/day)+anti-PD-L1 antibody) in the melanoma mouse model.

FIGS. 6A-6B show the effect of suppressing a tumor volume increase in the co-administration of Compound 1 and anti-CTLA-4 antibody, the control group (vehicle), the administration of Compound 1 alone, and the administration of anti-CTLA-4 antibody alone in the melanoma mouse model, and a difference in tumor volumes measured on day 15 after drug administration.

FIG. 7 shows changes in the body weights, during a period of the study, of the control group (vehicle), the administration group of Compound 1 alone, the administration group of anti-CTLA-4 antibody alone, and the co-administration group of Compound 1 and anti-CTLA-4 antibody in the melanoma mouse model.

FIGS. 8A-8B show the effect of suppressing a tumor volume increase in the co-administration of Compound 1 and anti-PD-1 antibody, the control group (vehicle), the administration of Compound 1 alone, and the administration of anti-PD-1 antibody alone in a colorectal cancer mouse model, and a difference in tumor weights measured on day 26 after drug administration.

FIGS. 9A-9B show the effect of suppressing a tumor volume increase in the co-administration of Compound 1 and anti-CTLA-4 antibody, the control group (vehicle), the administration of Compound 1 alone, and the administration of anti-CTLA-4 antibody alone in the colorectal cancer mouse model, and a difference in tumor volumes measured on day 26 after drug administration.

FIG. 10 shows the effect of suppressing a tumor volume increase in the co-administration of Compound 1, anti-PD-1 antibody, and anti-CTLA-4 antibody, the co-administration of Compound 1 and anti-CTLA-4 antibody, the control group (vehicle), the administration of Compound 1 alone, the administration of anti-PD-1 antibody alone, the administration of anti-CTLA-4 antibody alone, and the co-administration of anti-PD-1 antibody and anti-CTLA-4 antibody in the colorectal cancer mouse model.

FIG. 11 shows the effect of suppressing a tumor volume increase in the co-administration of Compound 1 and lenvatinib, the co-administration of Compound 1, lenvatinib, and anti-PD-1 antibody, a control group (vehicle), the administration of lenvatinib alone, the administration of the anti-PD-1 antibody alone, the co-administration of lenvatinib and anti-PD-1 antibody, and the administration of Compound 1 alone in the colorectal cancer mouse model.

FIG. 12 shows changes in tumor volumes, during a period of the study, of the control group (vehicle) and the study drug administration groups (anti-CTLA-4 antibody, lenvatinib, lenvatinib+anti-PD1 antibody, lenvatinib+anti-CTLA-4 antibody, Compound 1, Compound 1+anti-CTLA-4 antibody, and Compound 1+lenvatinib+anti-CTLA-4 antibody) in the colorectal cancer mouse model.

FIG. 13 shows changes in the body weights, during a period of the study, of the control (vehicle) and the study drug administration groups (Compound 1, lenvatinib, anti-CTLA-4 antibody, anti-PD1 antibody, Compound 1+anti-CTLA-4 antibody, Compound 1+anti-PD-1 antibody, Compound 1+lenvatinib, lenvatinib+anti-PD1 antibody, lenvatinib+anti-CTLA-4 antibody, anti-PD-1 antibody+anti-CTLA-4 antibody, Compound 1+lenvatinib+anti-PD-1 antibody, Compound 1+lenvatinib+anti-CTLA-4 antibody, Compound 1+anti-PD-1 antibody+anti-CTLA-4 antibody) in the colorectal cancer mouse model.

FIG. 14 shows the effect of suppressing a tumor volume increase in the co-administration of Compound 1 and anti-PD-1 antibody, a control group (vehicle), the administration of Compound 1 alone, and the administration of anti-PD-1 antibody alone in a sarcoma mouse model.

FIG. 15 shows the tumor remission rate in the co-administration of Compound 1 and anti-CTLA-4 antibody, the control group (vehicle), the administration of Compound 1, and the administration of anti-CTLA-4 antibody in the sarcoma mouse model.

FIG. 16 shows changes in the body weights, during a period of the study, of the control group (vehicle) and the study drug administration groups (anti-PD-1 antibody, Compound 1, anti-CTLA-4 antibody, Compound 1+anti-PD-1 antibody, and Compound 1+anti-CTLA-4 antibody) in the sarcoma mouse model.

FIGS. 17A-17B show the effect of suppressing a tumor volume increase in the co-administration of Compound 1 and anti-PD-1 antibody, a control group (vehicle), the administration of Compound 1 alone, and the administration of anti-PD-1 antibody alone in a breast carcinoma mouse model, and a difference in tumor volumes measured on day 23 after the cell line inoculation.

FIGS. 18A-18B show the effect of suppressing a tumor volume increase in the co-administration of Compound 1 and anti-CTLA-4 antibody, the control group (vehicle), the administration of Compound 1 alone, and the administration of anti-CTLA-4 antibody alone in the breast carcinoma mouse model, and a difference in tumor volumes measured on day 23 after the cell line inoculation.

FIG. 19 shows changes in the body weights, during a period of the study, of the control group (vehicle) and the study drug administration groups (anti-PD-1 antibody, Compound 1, anti-CTLA-4 antibody, Compound 1+anti-PD-1 antibody, and Compound 1+anti-CTLA-4 antibody) in the breast carcinoma mouse model.

FIGS. 20A-20B shows the survival rates of mice in the co-administration of Compound 1 and anti-PD-1 antibody, a control group (vehicle), the administration of Compound 1, and the administration of anti-PD-1 antibody in a bladder carcinoma mouse model.

FIG. 21 shows changes in the body weights, during a period of the study, of the control group and the study drug administration groups (Compound 1, anti-PD-1 antibody, and Compound 1+anti-PD-1 antibody) in the bladder carcinoma mouse model.

BEST MODE FOR CARRYING OUT THE INVENTION

An embodiment of the present invention relates to a pharmaceutical composition for preventing or treating a tumor, the pharmaceutical composition including a low-molecular kinase inhibitor that blocks the signaling pathway of transforming growth factor-β (TGF-β), in which the low-molecular kinase inhibitor that blocks the signaling pathway of TGF-β is administered in combination with at least one among an immune checkpoint regulator and a receptor tyrosine kinase inhibitor.

The term "low-molecular kinase inhibitor that blocks the signaling pathway of TGF-β" refers to a low-molecular kinase inhibitor that can inhibit the signaling pathway of TGF-β, such as a TGF-type I receptor kinase inhibitor, or a kinase inhibitor that dually inhibits a TGF-β type I receptor and vascular endothelial growth factor receptor (VEGFR)-2. Preferably, the low-molecular kinase inhibitor that blocks the signaling pathway of TGF-β may be a novel 2-pyridyl-substituted imidazole derivative, or a pharmaceutically acceptable salt or solvate thereof disclosed in Korean Patent No. 1938368. For example, the low-molecular kinase inhibitor that blocks the signaling pathway of TGF-β may be a compound or a pharmaceutically acceptable salt thereof selected from the group consisting of 1-[6-(6-methyl-pyridin-2-yl)-5-quinoxalin-6-yl-2,3-dihydro-imidazo[1,2-a]imidazol-1-yl]-ethanone, 6-[2-(6-methyl-pyridin-2-yl)-6,7-dihydro-5H-imidazo[1,2-a]imidazol-3-yl]-quinoxaline, 6-[2-(6-methyl-pyridin-2-yl)-5,6,7,8-tetrahydro-imidazo[1,2-a]pyrimidin-3-yl]-quinoxaline, 6-[2-(6-methyl-pyridin-2-yl)-6,7-dihydro-5H-imidazo[1,2-a]imidazol-3-yl]-quinoline, 6-[2-(6-methyl-pyridin-2-yl)-5,6,7,8-tetrahydro-imidazo[1,2-a]pyrimidin-3-yl]-quinoline, 2-[2-(6-methyl-pyridin-2-yl)-6,7-dihydro-5H-imidazo[1,2-a]imidazol-3-yl]-thieno[3,2-c]pyridine, 6-[2-(6-methyl-pyridin-2-yl)-6,7-dihydro-5H-imidazo[1,2-a]imidazol-3-yl]-benzothiazole, 5-benzo[b]thiophen-5-yl-6-(6-methyl-pyridin-2-yl)-2,3-dihydro-1H-imidazo[1,2-a]imidazole, 6-(6-methylpyridin-2-yl)-2,3-dihydro-1H-imidazo[1,2-a]imidazol-5-yl)-[1,2,4]triazole[1,5-a]pyridine, 5-[2-(6-methyl-pyridin-2-yl)-6,7-dihydro-5H-imidazo[1,2-a]imidazol-3-yl]-benzoxazole, 4-[2-(6-methyl-pyridin-2-yl)-6,7-dihydro-5H-imidazo[1,2-a]imidazol-3-yl]-quinoline, 5-benzo[1,3]dioxol-5-yl-6-(6-methyl-pyridin-2-yl)-2,3-dihydro-1H-imidazo[1,2-a]imidazole, 5-(2,3-dihydro-benzo[1,4]dioxin-6-yl)-6-(6-methyl-pyridin-2-yl)-2,3-dihydro-1H-imidazo[1,2-a]imidazole, 7-[2-(6-methyl-pyridin-2-yl)-6,7-dihydro-5H-imidazo[1,2-a]imidazol-3-yl]-2-pyrazol-1-yl-quinoxaline, dimethyl-(2-{7-[2-(6-methyl-pyridin-2-yl)-6,7-dihydro-5H-imidazo[1,2-a]imidazol-3-yl]-quinoxalin-2-yloxy}-ethyl)-amine, 2-methoxy-7-[2-(6-methyl-pyridin-2-yl)-6,7-dihydro-5H-imidazo[1,2-a]imidazol-3-yl]-quinoxaline, 5-(3,5-dimethoxyphenyl)-6-(6-methylpyridin-2-yl)-2,3-dihydro-1H-imidazo[1,2-a]imidazole, N,N-dimethyl-4-(6-(6-methylpyridin-2-yl)-2,3-dihydro-1H-imidazo[1,2-a]imidazol-5-yl)aniline, 4-(6-(6-methylpyridin-2-yl)-2,3-dihydro-1H-imidazo[1,2-a]imidazol-5-yl)benzonitrile, 2-methyl-6-(6-(6-methylpyridin-2-yl)-2,3-dihydro-1H-imidazo[1,2-a]imidazol-5-yl)quinoline, 4-(6-(6-methylpyridin-2-yl)-2,3-dihydro-1H-imidazo[1,2-a]imidazol-5-yl)aniline, N-(4-(6-(6-methylpyridin-2-yl)-2,3-dihydro-1H-imidazo[1,2-a]imidazol-5-yl)phenyl)acetamide, N-(4-(6-(6-methylpyridin-2-yl)-2,3-dihydro-1H-imidazo[1,2-a]imidazol-5-yl)phenyl)methanesulfonamide, tert-butyl (4-(6-(6-methylpyridin-2-yl)-2,3-dihydro-1H-imidazo[1,2-a]imidazol-5-yl)phenyl)carbamate, 5-(4-(4-methylpiperazin-1-yl)phenyl)-6-(6-methylpyridin-2-yl)-2,3-dihydro-1H-imidazo[1,2-a]imidazole, 4-(4-(6-(6-methylpyridin-2-yl)-2,3-dihydro-1H-imidazo[1,2-a]imidazol-5-yl)phenyl)morpholine, 6-(6-methylpyridin-2-yl)-5-(m-tolyl)-2,3-dihydro-1H-imidazo[1,2-a]imidazole, 5-(4-methoxyphenyl)-6-(6-methylpyridin-2-yl)-2,3-dihydro-1H-imidazo[1,2-a]imidazole, 6-(6-methylpyridin-2-yl)-5-(4-(trifluoromethyl)phenyl)-2,3-dihydro-1H-imidazo[1,2-a]imidazole, 6-(6-methylpyridin-2-yl)-5-(4-(methylthio)phenyl)-2,3-dihydro-1H-imidazo[1,2-a]imidazole, 5-(3-fluoro-4-methoxyphenyl)-6-(6-methylpyridin-2-yl)-2,3-dihydro-1H-imidazo[1,2-a]imidazole, 5-(4-fluorophenyl)-6-(6-methylpyridin-2-yl)-2,3-dihydro-1H-imidazo[1,2-a]imidazole, 1-acetyl-6-(6-methyl-pyridin-2-yl)-5-thieno[3,2-c]pyridin-2-yl-2,3-dihydro-1H-imidazo[1,2-a]imidazol-2-carboxylic acid ethyl ester, 6-(6-methyl-pyridin-2-yl)-5-thieno[3,2-c]pyridin-2-yl-2,3-dihydro-1H-imidazo[1,2-a]imidazol-2-carboxylic acid ethyl ester, [6-(6-methyl-pyridin-2-yl)-5-thieno[3,2-c]pyridin-2-yl-2,3-dihydro-1H-imidazo[1,2-a]imidazol-2-yl]-methanol, 1-acetyl-6-(6-methyl-pyridin-2-yl)-5-thieno[3,2-c]pyridin-2-yl-2,3-dihydro-1H-imidazo[1,2-a]imidazole-2-carbonitrile, 6-(6-methyl-pyridin-2-yl)-5-thieno[3,2-c]pyridin-2-yl-2,3-dihydro-1H-imidazo[1,2-a]imidazole-2-carbonitrile, 6-(6-methyl-pyridin-2-yl)-5-thieno[3,2-c]pyridin-2-yl-2,3-dihydro-1H-imidazo[1,2-a]imidazol-2-carboxylic acid amide, (6-(6-methylpyridin-2-yl)-5-(thieno[3,2-c]pyridin-2-yl)-2,3-dihydro-1H-imidazo[1,2-a]imidazol-2-yl)methanamine, and N-((6-(6-methylpyridin-2-yl)-5-(thieno[3,2-c]pyridin-2-yl)-2,3-dihydro-1H-imidazo[1,2-a]imidazol-2-yl)methyl)acetamide. More preferably, the low-molecular kinase inhibitor that blocks the signaling pathway of TGF-β may be a compound or a pharmaceutically acceptable salt thereof selected from the following compound group:

6-[2-(6-methyl-pyridin-2-yl)-6,7-dihydro-5H-imidazo[1,2-a]imidazol-3-yl]-quinoxaline; 6-[2-(6-methyl-pyridin-2-yl)-5,6,7,8-tetrahydro-imidazo[1,2-a]pyrimidin-3-yl]-quinoxaline; 6-[2-(6-methyl-pyridin-2-yl)-6,7-dihydro-5H-imidazo[1,2-a]imidazol-3-yl]-quinoline; 2-[2-(6-methyl-pyridin-2-yl)-6,7-dihydro-5H-imidazo[1,2-a]imidazol-3-yl]-thieno[3,2-c]pyridine; 6-[2-(6-methyl-pyridin-2-yl)-6,7-dihydro-5H-imidazo[1,2-a]imidazol-3-yl]-benzothiazole; 6-(6-(6-methylpyridin-2-yl)-2,3-dihydro-1H-imidazo[1,2-a]imidazol-5-yl)-[1,2,4]triazole[1,5-a]pyridine; and dimethyl-(2-{7-[2-(6-methyl-pyridin-2-yl)-6,7-dihydro-5H-imidazo[1,2-a]imidazol-3-yl]-quinoxalin-2-yloxy}-ethyl)-amine.

As used herein, the term "pharmaceutically acceptable salt" refers to a salt suitable for use in contact with human and animal tissues. Examples of suitable salts having such inorganic and organic acids include, but are not limited to, acetic acid, citric acid, formic acid, fumaric acid, hydrochloric acid, lactic acid, maleic acid, malic acid, methanesulfonic acid, nitric acid, phosphoric acid, p-toluenesulfonic acid, succinic acid, sulfuric acid, tartaric acid, trifluoroacetic acid, and the like. In addition, the pharmaceutically acceptable salt may be an acid- or base-addition salt formed by the reaction of an inorganic base such as sodium hydroxide, ammonium hydroxide, or potassium hydroxide, with an organic base such as mono-, di-, tri-alkyl, and aryl amines, or substituted ethanolamine.

In an embodiment of the present invention, the low-molecular kinase inhibitor that blocks the signaling pathway of TGF-β may be 6-[2-(6-methyl-pyridin-2-yl)-6,7-dihydro-5H-imidazo[1,2-a]imidazol-3-yl]-quinoxaline, 6-[2-(6-methyl-pyridin-2-yl)-5,6,7,8-tetrahydro-imidazo[1,2-a]pyrimidin-3-yl]-quinoxaline, 6-[2-(6-methyl-pyridin-2-yl)-6,7-dihydro-5H-imidazo[1,2-a]imidazol-3-yl]-quinoline, 2-[2-(6-methyl-pyridin-2-yl)-6,7-dihydro-5H-imidazo[1,2-a]imidazol-3-yl]-thieno[3,2-c]pyridine, 6-[2-(6-methyl-pyridin-2-yl)-6,7-dihydro-5H-imidazo[1,2-a]imidazol-3-yl]-benzothiazole, 6-(6-(6-methylpyridin-2-yl)-2,3-dihydro-1H-imidazo[1,2-a]imidazol-5-yl)-[1,2,4]triazole[1,5-a]pyridine, or dimethyl-(2-{7-[2-(6-methyl-pyridin-2-yl)-6,7-dihydro-5H-imidazo[1,2-a]imidazol-3-yl]-quinoxalin-2-yloxy}-ethyl)-amie.

Meanwhile, TGF-β is known to inhibit the proliferation of cells and induce apoptosis in a normal environment, but is present in a tumor microenvironment at a high concentration, while inhibiting immunity and promoting cancer cell metastasis, increasing the density and hardness of tumors through fibrosis of a cancer stroma and promoting angiogenesis, and blocking the delivery of anticancer drugs into tumor tissue and the infiltration of immune cells, thereby causing drug resistance. Therefore, the low-molecular kinase inhibitor that blocks the signaling pathway of TGF-β not only inhibits immune avoidance and metastasis of cancer cells, but also inhibits the fibrosis of tumor stroma caused by TGF-β and normalizes tumor vascular functions, thereby increasing intratumoral delivery of a drug used in combination and the infiltration rate of immune cells into tumors and also increasing oxygen concentration in a microenvironment around tumors. In addition, the low-molecular kinase inhibitor that blocks the signaling pathway of TGF-β of the present invention may be used in combination with various anticancer therapies/anticancer drugs such as an immune checkpoint regulator (e.g., a drug that inhibits immune checkpoint proteins to suppress regulatory T cells, a drug that binds to immune checkpoint proteins to activate effector T cells, etc.), chemotherapy, targeted therapeutics, nanoparticles, and radiotherapy. When the low-molecular kinase inhibitor that blocks the signaling pathway of TGF-β of the present invention is used in combination with an immune checkpoint regulator, it is possible to exhibit improved anticancer efficacy by increasing the infiltration rate of immune cells into tumors, the immune cells being targeted by the immune checkpoint regulator. In addition, when the low-molecular kinase inhibitor that blocks the signaling pathway of TGF-β of the present invention is used in combination with chemotherapy, targeted therapeutics, or nanoparticles, the low-molecular kinase inhibitor that blocks the signaling pathway of TGF-β may increase the efficiency of drug delivery and exhibit improved anti-cancer efficacy, and when the low-molecular kinase inhibitor that blocks the signaling pathway of TGF-β of the present invention is used in combination with radiotherapy, the low-molecular kinase inhibitor may increase the oxygen concentration in a tumor microenvironment and thus exhibit improved effects in treating/suppressing tumors.

An immune checkpoint refers to a group of signal molecules possessed by immune cells, and includes a signal molecule that may regulate and control the persistence of an immune response while maintaining self-tolerance, and is involved in an inhibitory pathway that maintains self-tolerance and aids the immune response, and a signal molecule that is involved in a stimulatory pathway. In addition, the effect of an immune response is determined by a subtle balance between a co-stimulatory signal and a co-inhibitory signal.

An immune checkpoint protein refers to both a protein involved in a pathway that inhibits an immune response and a protein involved in a pathway that activates an immune response. The immune checkpoint protein may be a protein involved in a signaling pathway that inhibits the activity of regulatory T cells or may be a protein involved in a signaling pathway that directly stimulates effector T cells or memory T cells. In addition, the immune checkpoint regulation may be to inhibit immune tolerance or activate the immune system, and may include inhibiting all signaling pathways that activate regulatory T cells involved in immune tolerance or stimulating signaling pathways that activate effector T cells or memory T cells in order to increase the anti-tumor immune response. Examples of immune checkpoint proteins include T cell receptors, and the T cell receptor proteins include, but are not limited to, programmed cell killing protein ligand 1 (PD-L1), programmed cell death protein 1 (PD-1), cytotoxic T-lymphocyte-associated antigen 4 (CTLA-4), B and T lymphocyte attenuator (BTLA), killer cell immunoglobulin-like receptor (KIR), lymphocyte activation gene 3 (LAG3), T-cell membrane protein 3 (corresponding to T-cell immunoglobulin mucin receptor 3: TIM3), OX40, V-domain immunoglobulin suppressor of T cell activation (VISTA), T cell immunoreceptor with immunoglobulin and ITIM domain (TIGIT), 4-1BB (CD137), Glucocorticoid-induced tumor necrosis factor related protein (GITR), adenosine A2a receptor (A2aR), and the like.

Accordingly, the immune checkpoint regulator may be an anti-immune checkpoint protein antibody or an antigen-binding fragment thereof, an aptamer, a fusion protein binding to the immune checkpoint protein, or a low-molecular compound that binds to the immune checkpoint protein or is involved in a mechanism related to inhibition or activation thereof.

In addition, the immune checkpoint regulator may be a material for regulating the signaling pathway in which an immune checkpoint protein selected from the group consisting of PD-L1, PD-1, CTLA-4, BTLA, KIR, LAG3, TIM3, OX40, VISTA, TIGIT, 4-1BB, GITR, and A2aR is involved. Further, the immune checkpoint regulator may be a substance that inhibits the signal transduction or reduces the expression of a T cell receptor selected from the group consisting of PD-L1, PD-1, CTLA-4, BTLA, KIR, LAG3, TIM3, OX40, VISTA, TIGIT, 4-1BB, GITR, and A2aR. Thus, the immune checkpoint regulator may inhibit regulatory T cells or activate effector T cells or memory T cells by inhibiting the signal transduction or reducing the expression through PD-L1, PD-1, CTLA-4, BTLA, KIR, LAG3, TIM3, OX40, VISTA, TIGIT, 4-1BB, GITR, A2aR, or a combination thereof. In addition, the immune checkpoint regulator may be a PD-L1 inhibitor, a PD-1 inhibitor, a CTLA-4 inhibitor, an OX40 agonist, or a combination thereof.

Specifically, the immune checkpoint regulator may be at least one selected from among at least one selected from the group consisting of an aptamer, a peptide, an antibody, and an antigen-binding fragment of the antibody, which specifically bind to the PD-L1 protein; at least one selected from the group consisting of an aptamer, a peptide, an antibody, and an antigen-binding fragment of the antibody, which specifically bind to the PD-1 protein; at least one selected from the group consisting of an aptamer, a peptide, an antibody, and an antigen-binding fragment of the antibody, which specifically bind to the OX40 protein; and at least one selected from the group consisting of an aptamer, a peptide, an antibody, and an antigen-binding fragment of the antibody, which specifically bind to the CTLA-4 protein. More specifically, the immune checkpoint regulator may be an anti-PD-L1 antibody or an antigen-binding fragment thereof; an anti-PD-1 antibody or an antigen-binding fragment thereof; an anti-OX40 antibody or an antigen-binding fragment thereof; or an anti-CTLA-4 antibody or an antigen-binding fragment thereof.

The PD-L1 inhibitor may be a neutralizing antibody or an antigen-binding fragment thereof, an aptamer, which binds to PD-L1, or a fusion protein including an antibody capable of binding to PD-L1, or may be a low-molecular compound that inhibits the function of PD-L1, but is not limited thereto. Examples of the PD-L1 inhibitor include, but are not limited to, BMS-936559 (MDX1105, Bristol Myers Squibb), MEDI4736 (MedImmune, AstraZeneca), MPDL3280A (Roche), CK-301 (Checkpoint Therapeutica), MSB0010718C (Merck), and the like.

The PD-1 inhibitor may be a neutralizing antibody or an antigen-binding fragment thereof, an aptamer, which binds to PD-1, or a fusion protein including an antibody capable of binding to PD-1, or may be a low-molecular compound that inhibits the function of PD-1, but is not limited thereto. Examples of the PD-1 inhibitor include, but are not limited to, AMP-224 (Amplimmune, GlaxoSmith Klein), AMP-514 (MEDI0680, Amplimmune, GlaxoSmith Klein), nivolumab (Opdivo, Bristol Myers Squibb), pembrolizumab (Keytruda, Merck), pidilizumab (Cure Tech), BGB-A317 (BeiGene, Celgene), PF-06801591 (Pfizer), PDR001 (Novartis), TSR-042 (Tesaro, GlaxoSmithKline), MGA012 (Incyte/MacroGenics), IBI308 (Innovent, Eli Lilly), BI 754091 (Boehringer Ingelheim), and the like.

The CTLA-4 inhibitor may be a neutralizing antibody or an antigen-binding fragment thereof, an aptamer, which binds to CTLA-4, or a fusion protein including an antibody capable of binding to CTLA-4, or may be a low-molecular compound that inhibits the function of CTLA-4, but is not limited thereto. Examples of the CTLA-4 inhibitor include, but are not limited to, ipilimumab (Yervoy, Bristol Myers Squibb), tremelimumab (Pfizer), and the like.

The OX40 agonist may be a neutralizing antibody or an antigen-binding fragment thereof, an aptamer, which binds to OX40, or a fusion protein including an antibody capable of binding to OX40, or a low-molecular compound that activates the function of OX40, but is not limited thereto. Examples of the OX40 agonist include, but are not limited to, ABBV-368 (Abbvie), GSK3174998 (GlaxoSmithKline), MOXR0916 (Genentech), INCAGN01949 (Incyte Biosciences International), IBI101 (Innovent), BMS-986178 (Bristol Myers Squibb), PF-04518600 (Pfizer), and the like.

As used herein, the term "receptor tyrosine kinase" refers to a receptor that is a transmembrane protein that penetrates a cell membrane and is responsible for a cell signaling system that regulates cell proliferation, cell migration, cell cycle, and cell differentiation. Furthermore, as used herein, the term "receptor tyrosine kinase inhibitor" may be an anti-receptor tyrosine kinase antibody or an antigen-binding fragment thereof, an aptamer, a fusion protein that binds to a receptor tyrosine kinase protein, or a low-molecular compound that binds to a receptor tyrosine kinase protein or is involved in a mechanism related to inhibition. In addition, the receptor tyrosine kinase inhibitor may be an inhibitor of at least one tyrosine kinase selected from among a VEGF receptor, an FGF receptor, PDGFR α, KIT, RET, and c-Met. Specifically, the receptor tyrosine kinase inhibitor may be an antibody or an antigen-binding fragment thereof, an aptamer, which binds to at least one tyrosine kinase selected from among a VEGF receptor, an FGF receptor, PDGFR α, KIT, RET, and c-Met, or a fusion protein including an antibody capable of binding to the tyrosine kinase, or may be a low-molecular compound that selectively inhibits the tyrosine kinase. In addition, the receptor tyrosine kinase inhibitor may be a compound that inhibits the function of at least one tyrosine kinase selected from among a VEGF receptor, an FGF receptor, PDGFR α, KIT, RET, and c-Met, or may be at least one selected from among an aptamer, a peptide, an antibody, and an antigen-binding fragment of the antibody, which specifically bind to the tyrosine kinase protein, and includes, but is not limited to, cabozantinib, lenvatinib, vandetanib, selpercatinib, pralsetinib, and the like.

Meanwhile, as used herein, the term "antibody" may be a neutralizing antibody having the ability to neutralize a target protein.

As used herein, the term "pharmaceutical composition" encompasses any product resulting from combining components specified in a directly or indirectly specified amount as well as a product including a specified component in a predetermined amount or ratio. In particular, this encompasses any carrier including one or more active ingredients, and an inert ingredient, as well as any product resulting directly or indirectly from a combination, complexation or aggregation of any two or more ingredients, or from decomposition of one or more ingredients, or from interaction of one or more ingredients or other types of reactions.

As used herein, the term "tumor" refers to a cellular disorder characterized by uncontrolled or dysregulated cell proliferation, decreased cell differentiation, inappropriate ability to invade surrounding tissue, and/or the ability to establish new growth at ectopic sites. In addition, tumors include, but are not limited to, solid tumors and blood-borne tumors, and further include diseases of skin, tissues, organs, bone, cartilage, blood and blood vessels, or primary and metastatic tumors.

In addition, tumors include, but are not limited to, (1) leukemia including, but not limited to, acute leukemia, acute lymphocytic leukemia, acute myelocytic leukemia, such as myeloblast leukemia, promyelocytic leukemia, myelomonocytic leukemia, monocytic leukemia, erythroleukemia, myelodysplastic syndrome, proleukemia, and chronic myelomonocytic leukemia (CMML), (2) chronic leukemia including, but not limited to, chronic myelocytic (granulocytic) leukemia, chronic lymphocytic leukemia, and hairy cell leukemia; (3) lymphoma including, but not limited to, Hodgkin's disease and non-Hodgkin's disease; (4) multiple myeloma including, but not limited to, smoldering multiple myeloma, nonsecretory myeloma, osteosclerotic myeloma, plasma cell leukemia, solitary plasmacytoma, and extramedullary plasmacytoma; (5) bone and connective tissue sarcomas including, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma, fibrosarcoma, Kaposi's sarcoma, leiomyosarcoma, liposarcoma, lymphangiosarcoma, metastatic cancer, neurilemmoma, rhabdomyosarcoma, and synovial sarcoma; (6) brain tumors including, but not limited to, glioma, glioblastoma, astrocytoma, brain stem glioma, ependymoma, oligodendroglioma, nonglial tumor, acoustic neurinoma, craniopharyngioma, medulloblastoma, meningioma, pineocytoma, pineoblastoma, oligodendroblastoma, and primary brain lymphoma; (7) breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; (8) adrenal cancer including, but not limited to, pheochromocytoma and adrenocortical carcinoma; (9) thyroid cancer including, but not limited to, papillary or follicular thyroid cancer, medullary thyroid cancer, and anaplastic thyroid cancer; (10) pancreatic cancer including, but not limited to, insulinoma, gastrinoma, glucagonoma, vipoma, somatostatin-secreting tumor, and carcinoid or islet cell tumor; (11) pituitary cancers including, but not limited to, Cushing's disease, prolactin-secreting tumor, acromegaly, and diabetes insipidus; (12) eye cancers including, but not limited to, ocular melanoma such as iris melanoma, choroidal melanoma, and ciliary body melanoma, and retinoblastoma; (13) vaginal cancers including, but not limited to, squamous cell carcinoma, adenocarcinoma, and melanoma; (14) vulvar cancer including, but not limited to, squamous cell carcinoma, melanoma, adenocarcinoma, basal cell carcinoma, sarcoma, and Paget's disease; (15) cervical cancers including, but not limited to, squamous cell carcinoma, and adenocarcinoma; (16) endometrial carcinoma, (17) uterine cancers including, but not limited to, uterine sarcoma; (18) ovarian cancers including, but not limited to, ovarian epithelial carcinoma, borderline tumor, germ cell tumor, and stromal tumor; (19) esophageal cancers including, but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; (20) stomach cancers including, but not limited to, adenocarcinoma, fungating (polypoid), ulcerating, superficial spreading, diffusely spreading, malignant lymphoma, liposarcoma, fibrosarcoma, and carcinosarcoma; (21) colon cancers; (22) rectal cancers; (23) liver cancers including, but not limited to, hepatocellular carcinoma and hepatoblastoma; (24) gallbladder cancers including, but not limited to, adenocarcinoma; (25) cholangiocarcinomas including, but not limited to, papillary, nodular, and diffuse; (26) lung cancers including, but not limited to, non-small cell lung cancer, squamous cell carcinoma (epidermoid carcinoma), adenocarcinoma, large-cell carcinoma, and small-cell lung cancer; (27) testicular cancers including, but not limited to, germinal tumor, seminoma, anaplastic, classic (typical), spermatocytic, nonseminoma, embryonal carcinoma, teratoma carcinoma, choriocarcinoma (yolk-sac tumor); (28) prostate cancers including, but not limited to, adenocarcinoma, leiomyosarcoma, and rhabdomyosarcoma; (29) penile cancers; (30) oral cancers including, but not limited to, larynx cancer, pharynx cancer, nasopharynx cancer, oropharynx cancer, and squamous cell carcinoma; (31) basal cancers; (32) salivary gland cancers including, but not limited to, adenocarcinoma, mucoepidermoid carcinoma, and adenoidcystic carcinoma; (33) pharynx cancers including, but not limited to, squamous cell cancer, and verrucous; (34) skin cancers including, but not limited to, basal cell carcinoma, squamous cell carcinoma and melanoma, superficial spreading melanoma, nodular melanoma, lentigo malignant melanoma, acral lentiginous melanoma; (35) kidney cancers including, but not limited to, renal cell cancer, adenocarcinoma, hypernephroma, fibrosarcoma, transitional cell cancer (renal pelvis and/or ureter); (36) Wilms' tumor; (37) bladder cancers including, but not limited to, transitional cell carcinoma, squamous cell cancer, adenocarcinoma, carcinosarcoma; (38) head and neck cancers (including mouth, nose, throat, larynx, sinus or salivary gland cancer, head and neck squamous cell carcinoma); (39) hepatocellular carcinoma; and (40) appendix cancers, bronchial cancers, chorionic carcinoma, chordoma, ependymoma, gastrointestinal stromal tumor (GIST), neuroendocrine cancers (e.g., gastroenteropancreatic neuroendocrine tumor (GEP-NET), Carcinoma of Cancer), malignant peripheral nerve sheath tumor (MPNST), and urethral cancers, but other cancers not included thereto (see Fishman et al., 1985, Medicine, 2nd Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America). Meanwhile, the tumor may be a metastatic tumor, an unresectable tumor, or a locally advanced tumor. In addition, the tumor may be selected from the group consisting of melanoma, sarcoma, brain tumor, breast cancer, adrenal cancer, thyroid cancer, pancreatic cancer, pituitary carcinoma, glioblastoma, ocular cancer, vaginal cancer, vulvar cancer, cervical cancer, endometrial carcinoma, uterine cancer, ovarian cancer, esophageal cancer, stomach cancer, colon cancer, rectal cancer, liver cancer, gallbladder cancer, cholangiocarcinoma, lung cancer, testicular cancer, prostate cancer, penile cancer, oral cancer, basal cancer, salivary gland cancer, pharynx cancer, skin cancer, kidney cancer, Wilms' tumor, bladder cancer, head and neck cancer, head and neck squamous cell carcinoma, hepatocellular carcinoma, appendix cancer, bronchial cancer, chorial carcinoma, chordoma, ependymoma, gastrointestinal stromal tumor (GIST), neuroendocrine cancer, and urethral cancer. In an embodiment of the present invention, the tumor may be a solid tumor.

As used herein, the term "prevention" refers to all actions embodiment inhibit cancer or delay the onset of cancer, and the term "treatment" refers to all actions in which symptoms of cancer are improved or beneficially changed.

As used herein, the term "subject" refers to an animal, preferably a mammal, and most preferably a human.

In an embodiment of the present invention, a subject in need of the treatment of a tumor or the inhibition of tumor growth may be, but is not limited to, a subject at risk of developing or experiencing tumor recurrence. In another embodiment of the present invention, a subject in need of the treatment of a tumor or the inhibition of tumor growth may be a subject that has been treated with at least one anticancer therapy selected from surgery, radiotherapy, and chemotherapy, but is not limited thereto. In addition, a subject in need of the treatment of a tumor or the inhibition of tumor growth may be a subject that has been administered at least one chemotherapy selected from the group consisting of a receptor tyrosine kinase inhibitor and an immune checkpoint regulator.

It should be understood that when the terms "in combination," "a combination," or "combined administration" are used herein, it includes administering a low-molecular kinase inhibitor that blocks the signaling pathway of TGF-β in combination with an immune checkpoint regulator and/or receptor tyrosine kinase inhibitor simultaneously or separately at different time points. When the low-molecular kinase inhibitor, the immune checkpoint regulator, and/or the receptor tyrosine kinase inhibitor, which blocks the signaling pathway of TGF-β, are individually administered, the administration cycles thereof may be different from each other, and the administration routes thereof may be different from each other.

As used herein, the term "pharmaceutically acceptable" refers to a substance that is biologically or otherwise not undesirable, i.e., a substance that may be administered to a subject with a composition that does not cause any undesirable biological effect or interact in a harmful manner with any other component of a pharmaceutical composition containing it.

As used herein, the term "pharmaceutically acceptable carrier" refers to a carrier and an auxiliary substance compatible with other components of a formulation, such as a diluent or an excipient. Examples of pharmaceutically acceptable carriers include, but are not limited to, saline, Ringer's solution, and dextrose solution. The carrier will be chosen to minimize any degradation of the active ingredient, and to minimize any adverse effects on the subject, as well known to those skilled in the art. The pH of the solution is preferably from about 5 to 8, more preferably from about 7 to about 7.5. The carrier includes a sustained release preparation, such as semipermeable matrices of a solid hydrophobic polymer containing antibodies, in which the matrix thereof is in the form of shaped articles, e.g., films, liposomes, or microparticles. It will be apparent to those skilled in the art that some carriers would more preferably depend on, for example, the route and concentration of administration of the composition to be administered. In addition, pharmaceutically acceptable carriers are known to those skilled in the art and most of them will typically be standard carriers for administering drugs to humans, including solutions such as sterile water, saline and buffer solutions with physiological pH.

Also, in another embodiment of the present invention, the pharmaceutical composition of the present invention may include thickeners, diluents, buffers, preservatives, surface active agents, and the like.

Pharmaceutical compositions for parenteral injection include a pharmaceutically acceptable sterile aqueous solution or a non-aqueous solution, dispersion, suspension or emulsion, as well as sterile powders for the reconstitution into sterile injectable solutions or dispersions just prior to use. Examples of suitable aqueous and non-aqueous carriers, diluents, solvents, or vehicles include water, ethanol, glycerol, polyols (such as propylene glycol, polyethylene glycol, or the like), carboxymethylcellulose, and suitable mixtures thereof, vegetable oils (such as olive oils), and injectable organic esters such as ethyl oleates. Proper fluidity can be maintained, for example, by the use of coating materials, such as lecithin, by the maintenance of the required particle size in the case of dispersions, and by the use of surfactants. These compositions may also contain preservatives, wetting agents, emulsifying agents, and dispersing agents. Prevention of microbial action may be ensured by the inclusion of various antimicrobial and antifungal agents such as paraben, chlorobutanol, phenol sorbic acid, and the like. It may also be desirable to include isotonic agents, such as sugars, sodium chloride, and the like. Prolonged absorption of the injectable pharmaceutical form maybe brought about by the inclusion of agents which delay absorption such as aluminum monostearate and gelatin. Injectable depot forms are made by forming microencapsule matrices of the drugs in biodegradable polymers such as polylactide-polyglycolide, poly(orthoesters), and poly(anhydrides). Depending on the ratio of drug to polymer, and the nature of the particular polymer employed, the rate of drug release can be controlled. Depot injectable formulations are also prepared by entrapping the agent in liposomes or microemulsions which are compatible with body tissue. The injectable formulations may be sterilized by, for example, filtration through a bacteria-retaining filter, or by incorporating sterilizing agents in the form of sterile solid compositions which can be dissolved in sterile water, or some other sterile injectable medium immediately before use.

Pharmaceutical compositions for oral administration may be in the form of, for example, tablets, lozenges, aqueous or oily suspensions, granules, powders, emulsions, capsules, syrups or elixirs. Orally administered pharmaceutical compositions may contain one or more optional agents, for example, sweetening agents such as fructose, aspartame or saccharin; flavoring agents such as peppermint, oil of wintergreen, or cherry coloring agents and preserving agents, to provide a pharmaceutically palatable preparation. Moreover, in tablet or pill form, the compositions may be coated to delay disintegration and absorption in the gastrointestinal tract, thereby providing a sustained action over an extended period of time. Selectively permeable membranes surrounding an osmotically active driving compound are also suitable for orally administered compounds of the present invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions may include standard vehicles such as mannitol, lactose, starch, magnesium stearate, sodium saccharine, cellulose, magnesium carbonate, etc. Such vehicles are preferably of pharmaceutical grade.

For oral liquid pharmaceutical compositions, preparations, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate between about 5.0 mM to about 50.0 mM) etc. In addition, flavoring agents, preservatives, coloring agents, bile salts, acylcarnitines and the like may be added. In addition, in an aspect of the present invention, the pharmaceutical composition for oral administration may take the form of tablets, capsules, and the like formulated in a conventional manner.

In the present invention, a therapeutically effective amount of a low-molecular kinase inhibitor that blocks the signaling pathway of TGF-β refers to at least a minimum dose of the low-molecular kinase inhibitor disclosed herein necessary to achieve a desired therapeutic effect and includes a dose sufficient to reduce tumor symptoms, tumor growth, and the like. In addition, a therapeutically effective amount of an immune checkpoint regulator and a receptor tyrosine kinase inhibitor refer to at least a minimum dose of the immune checkpoint regulator and the receptor tyrosine kinase inhibitor disclosed herein necessary to achieve the desired therapeutic effect, and include a dose sufficient to reduce tumor symptoms, tumor growth, and the like. The effectiveness of a combination of the low-molecular kinase inhibitor with at least one selected from among the immune checkpoint regulator and the receptor tyrosine kinase inhibitor disclosed herein in treating a tumor can be determined by observing an improvement in a subject based on one or more clinical symptoms and/or physiological indicators associated with the condition. An improvement in tumor can also be indicated by a reduced need for a concurrent therapy.

In another embodiment of the present invention, the low-molecular kinase inhibitor that blocks the signaling pathway of TGF-β may be administered once daily, twice daily, or trice daily, but is not limited thereto. Preferably, the low-molecular kinase inhibitor that blocks the signaling pathway of TGF-β may be administered twice daily in the same dose or in different doses. More preferably, the low-molecular kinase inhibitor that blocks the signaling pathway of TGF-β may be administered twice daily in the same dose.

In an embodiment of the present invention, the low-molecular kinase inhibitor, the immune checkpoint regulator, and the receptor tyrosine kinase inhibitor may each independently be administered to a subject in need of treatment through topically, parenterally, orally, intravenously, intramuscularly, subcutaneously administration, or by aerosol, but is not limited thereto.

In an embodiment of the present invention, the low-molecular kinase inhibitor that blocks the signaling pathway of TGF-β may be administered in combination with the immune checkpoint regulator.

In another embodiment of the invention, the low-molecular kinase inhibitor that blocks the signaling pathway of TGF-β may be administered in combination with the receptor tyrosine kinase inhibitor.

In another embodiment of the invention, the low-molecular kinase inhibitor that blocks the signaling pathway of TGF-β may be administered in combination with the receptor tyrosine kinase inhibitor and the immune checkpoint regulator.

In an embodiment of the invention, the low-molecular kinase inhibitor that blocks the signaling pathway of TGF-β, the immune checkpoint regulator, and the receptor tyrosine kinase inhibitor are each contained as an active ingredient in different formulations and may be administered simultaneously or at different times. Specifically, the low-molecular kinase inhibitor that blocks the signaling pathway of TGF-β, the immune checkpoint regulator, and the receptor tyrosine kinase inhibitor may be administered separately at different times.

In addition, in another aspect of the present invention, the low-molecular kinase inhibitor may be orally administered.

Furthermore, the immune checkpoint regulator and the receptor tyrosine kinase inhibitor may be administered according to known administration methods, dosage, and administration cycles of the corresponding immune checkpoint regulator and the receptor tyrosine kinase inhibitor in the art to which the present invention pertains.

In another embodiment of the present invention, the present invention may be a pharmaceutical composition for treating a tumor, the pharmaceutical composition including a low-molecular kinase inhibitor that blocks the signaling pathway of TGF-β in order to treat a tumor patient which has been administered an immune checkpoint regulator and/or a receptor tyrosine kinase inhibitor.

In another embodiment of the present invention, the present invention may be a pharmaceutical composition for treating a tumor, the pharmaceutical composition including a low-molecular kinase inhibitor that blocks the signaling pathway of TGF-β, wherein the low-molecular kinase inhibitor that blocks the signaling pathway of TGF-β is administered in combination with at least one selected from among an immune checkpoint regulator and a receptor tyrosine kinase inhibitor, thereby increasing the action of the immune checkpoint regulator and/or the receptor tyrosine kinase inhibitor or increasing the action of the low-molecular kinase inhibitor that blocks the signaling pathway of TGF-β.

In an embodiment of the present invention, the present invention may be a combination or pharmaceutical composition for preventing or treating a tumor, the combination or pharmaceutical composition including a low-molecular kinase inhibitor that blocks the signaling pathway of TGF-β, and at least one among an immune checkpoint regulator and a receptor tyrosine kinase inhibitor. In this case, the low-molecular kinase inhibitor that blocks the signaling pathway of TGF-β, the immune checkpoint regulator, and the receptor tyrosine kinase inhibitor may be administered simultaneously, sequentially, or separately, and the types of the low-molecular kinase inhibitor that blocks the signaling pathway of TGF-β, the immune checkpoint regulator, and the receptor tyrosine kinase inhibitor, the tumor types, the administration methods, and doses thereof are as defined above.

As used herein, the term "a combination" refers to a product produced by mixing or blending two or more active ingredients, and includes both fixed and non-fixed combinations of the active ingredients. The term "fixed combination" means that active ingredients, e.g., a low-molecular kinase inhibitor that blocks the signaling pathway of TGF-β, and at least one selected from among an immune checkpoint regulator, and a receptor tyrosine kinase inhibitor, are all administered to a patient simultaneously in the form of a single entity or dosage. The term "non-fixed combination" means that active ingredients, e.g., a low-molecular kinase inhibitor that blocks the signaling pathway of TGF-β, and at least one selected from among an immune checkpoint regulator, and a receptor tyrosine kinase inhibitor, are administered to a subject as separate entities either concurrently, simultaneously, or sequentially with no specific time limits, wherein such administration provides therapeutically effective levels of the active ingredients in the body of the patient. The non-fixed combination also applies to cocktail therapy, e.g., the administration of three or more active ingredients.

In an embodiment of the present invention, the pharmaceutical composition or combination of the present invention may be a pharmaceutical composition or combination for preventing or treating melanoma, colorectal cancer, bladder cancer, sarcoma, breast cancer, cervical cancer, head and neck squamous cell carcinoma, or liver cancer, including 6-(6-(6-methylpyridin-2-yl)-2,3-dihydro-1H-imidazo[1,2-a]imidazol-5-yl)-[1,2,4]triazole[1,5-a]pyridine or a pharmaceutically acceptable salt thereof, which may be administered in combination with a PD-1 inhibitor (preferably an anti-PD-1 antibody or fragment thereof).

In an embodiment of the present invention, the pharmaceutical composition or combination of the present invention may be a pharmaceutical composition or combination for preventing or treating melanoma, including 6-(6-(6-methylpyridin-2-yl)-2,3-dihydro-1H-imidazo[1,2-a]imidazol-5-yl)-[1,2,4]triazole[1,5-a]pyridine or a pharmaceutically acceptable salt thereof, which may be administered in combination with a PD-L1 inhibitor (preferably an anti-PD-L1 antibody or fragment thereof).

In another embodiment of the present invention, the pharmaceutical composition or combination of the present invention may be a pharmaceutical composition or combination for preventing or treating melanoma, colorectal cancer, sarcoma, breast cancer, cervical cancer, head and neck squamous cell carcinoma, or liver cancer, including 6-(6-(6-methylpyridin-2-yl)-2,3-dihydro-1H-imidazo[1,2-a]imidazol-5-yl)-[1,2,4]triazole[1,5-a]pyridine or a pharmaceutically acceptable salt thereof, which may be administered in combination with a CTLA-4 inhibitor (preferably an anti-CTLA-4 antibody or fragment thereof).

In another embodiment of the present invention, the pharmaceutical composition or combination of the present invention may be a pharmaceutical composition or combination for preventing or treating colorectal cancer, cervical cancer, head and neck squamous cell carcinoma, or liver cancer, including 6-(6-(6-methylpyridin-2-yl)-2,3-dihydro-1H-imidazo[1,2-a]imidazol-5-yl)-[1,2,4]triazole[1,5-a]pyridine or a pharmaceutically acceptable salt thereof, which may be administered in combination with lenvatinib.

In an embodiment of the present invention, the pharmaceutical composition or combination of the present invention may be a pharmaceutical composition or combination for preventing or treating colorectal cancer, cervical cancer, head and neck squamous cell carcinoma, or liver cancer, including 6-(6-(6-methylpyridin-2-yl)-2,3-dihydro-1H-imidazo[1,2-a]imidazol-5-yl)-[1,2,4]triazole[1,5-a]pyridine or a pharmaceutically acceptable salt thereof, which may be administered in combination with lenvatinib and a PD-1 inhibitor (preferably an anti-PD-1 antibody or fragment thereof).

In another embodiment of the present invention, the pharmaceutical composition or combination of the present invention may be a pharmaceutical composition or combination for preventing or treating colorectal cancer, cervical cancer, head and neck squamous cell carcinoma, or liver cancer, including 6-(6-(6-methylpyridin-2-yl)-2,3-dihydro-1H-imidazo[1,2-a]imidazol-5-yl)-[1,2,4]triazole[1,5-a]pyridine or a pharmaceutically acceptable salt thereof, which may be administered in combination with lenvatinib and a CTLA-4 inhibitor (preferably an anti-CTLA-4 antibody or fragment thereof).

In an embodiment of the present invention, the pharmaceutical composition or combination of the present invention may be a pharmaceutical composition or combination for preventing or treating colorectal cancer, cervical cancer, head and neck squamous cell carcinoma, or liver cancer, including 6-(6-(6-methylpyridin-2-yl)-2,3-dihydro-1H-imidazo[1,2-a]imidazol-5-yl)-[1,2,4]triazole[1,5-a]pyridine or a pharmaceutically acceptable salt thereof, which may be administered in combination with a PD-1 inhibitor (preferably, an anti-PD-1 antibody or fragment thereof) and a CTLA-4 inhibitor (preferably, an anti-CTLA-4 antibody or fragment thereof).

In another embodiment of the present invention, the present invention may be a method for preventing or treating a tumor in a subject, the method including administering to the subject a low-molecular kinase inhibitor that blocks the signaling pathway of TGF-β, and at least one among an immune checkpoint regulator and a receptor tyrosine kinase inhibitor. In this case, the low-molecular kinase inhibitor that blocks the signaling pathway of TGF-β, the immune checkpoint regulator, and the receptor tyrosine kinase inhibitor may be administered simultaneously, sequentially, or separately, and the types of the low-molecular kinase inhibitor that blocks the signaling pathway of TGF-β, the immune checkpoint regulator, and the receptor tyrosine kinase inhibitor, the tumor types, the administration methods, and doses thereof are as defined above.

In an embodiment of the present invention, the present invention may be a method for preventing or treating melanoma, colorectal cancer, bladder cancer, sarcoma, breast cancer, cervical cancer, head and neck squamous cell carcinoma, or liver cancer in a subject, the method including administering to the subject 6-(6-(6-methylpyridin-2-yl)-2,3-dihydro-1H-imidazo[1,2-a]imidazol-5-yl)-[1,2,4]triazol[1,5-a]pyridine or a pharmaceutically acceptable salt thereof and a PD-1 inhibitor (preferably an anti-PD-1 antibody or fragment thereof).

In an embodiment of the present invention, the present invention may be a method for preventing or treating melanoma in a subject, the method including to the subject 6-(6-(6-methylpyridin-2-yl)-2,3-dihydro-1H-imidazo[1,2-a]imidazol-5-yl)-[1,2,4]triazole[1,5-a]pyridine or a pharmaceutically acceptable salt thereof and a PD-L1 inhibitor (preferably an anti-PD-L1 antibody or fragment thereof).

In another embodiment of the present invention, the present invention may be a method for preventing or treating melanoma, colorectal cancer, sarcoma, breast cancer, cervical cancer, head and neck squamous cell carcinoma, or liver cancer in a subject, the method including administering to the subject 6-(6-(6-methylpyridin-2-yl)-2,3-dihydro-1H-imidazo[1,2-a]imidazol-5-yl)-[1,2,4]triazol[1,5-a]pyridine or a pharmaceutically acceptable salt thereof and a CTLA-4 inhibitor (preferably an anti-CTLA-4 antibody or fragment thereof).

In another embodiment of the present invention, the present invention may be a method for preventing or treating colorectal cancer, cervical cancer, head and neck squamous cell carcinoma or liver cancer in a subject, the method including administering to the subject 6-(6-(6-methylpyridin-2-yl)-2,3-dihydro-1H-imidazo[1,2-a]imidazol-5-yl)-[1,2,4]triazole[1,5-a]pyridine or a pharmaceutically acceptable salt thereof and lenvatinib.

In an embodiment of the present invention, the present invention may be a method for preventing or treating colorectal cancer, cervical cancer, head and neck squamous cell carcinoma, or liver cancer in a subject, the method including administering to the subject 6-(6-(6-methylpyridin-2-yl)-2,3-dihydro-1H-imidazo[1,2-a]imidazol-5-yl)-[1,2,4]triazol[1,5-a]pyridine or a pharmaceutically acceptable salt thereof, lenvatinib, and a PD-1 inhibitor (preferably an anti-PD-1 antibody or fragment thereof).

In another embodiment of the present invention, the present invention may be a method for preventing or treating colorectal cancer, cervical cancer, head and neck squamous cell carcinoma, or liver cancer in a subject, the method including administering to the subject 6-(6-(6-methylpyridin-2-yl)-2,3-dihydro-1H-imidazo[1,2-a]imidazol-5-yl)-[1,2,4]triazol[1,5-a]pyridine or a pharmaceutically acceptable salt thereof, lenvatinib, and a CTLA-4 inhibitor (preferably an anti-CTLA-4 antibody or fragment thereof).

In an embodiment of the present invention, the present invention may be a method for preventing or treating colorectal cancer, cervical cancer, head and neck squamous cell carcinoma, or liver cancer in a subject, the method including administering to the subject 6-(6-(6-methylpyridin-2-yl)-2,3-dihydro-1H-imidazo[1,2-a]imidazol-5-yl)-[1,2,4]triazol[1,5-a]pyridine or a pharmaceutically acceptable salt thereof, a PD-1 inhibitor (preferably, an anti-PD-1 antibody or fragment thereof), and a CTLA-4 inhibitor (preferably, an anti-CTLA-4 antibody or fragment thereof).

In addition, in another embodiment of the present invention, the present invention relates to a use of a low-molecular kinase inhibitor that blocks the signaling pathway of TGF-β, which is administered in combination with at least one among an immune checkpoint regulator and a receptor tyrosine kinase inhibitor for preparing a medicament for preventing or treating a tumor. In this case, the low-molecular kinase inhibitor that blocks the signaling pathway of TGF-β, the immune checkpoint regulator, and the receptor tyrosine kinase inhibitor may be administered simultaneously, sequentially, or separately, and the types of the low-molecular kinase inhibitor that blocks the signaling pathway of TGF-β, the immune checkpoint regulator, and the receptor tyrosine kinase inhibitor, the tumor types, the administration methods, and doses thereof are as defined above.

In an embodiment of the present invention, the present invention may be a use of 6-(6-(6-methylpyridin-2-yl)-2,3-dihydro-1H-imidazo[1,2-a]imidazol-5-yl)-[1,2,4]triazol[1,5-a]pyridine or a pharmaceutically acceptable salt thereof, which is administered in combination with a PD-1 inhibitor (preferably an anti-PD-1 antibody or fragment thereof) for preparing a medicament for preventing or treating melanoma, colorectal cancer, bladder cancer, sarcoma, breast cancer, cervical cancer, head and neck squamous cell carcinoma, or liver cancer.

In an embodiment of the present invention, the present invention may be a use of 6-(6-(6-methylpyridin-2-yl)-2,3-dihydro-1H-imidazo[1,2-a]imidazol-5-yl)-[1,2,4]triazol[1,5-a]pyridine or a pharmaceutically acceptable salt thereof, which is administered in combination with a PD-L1 inhibitor (preferably an anti-PD-L1 antibody or fragment thereof) for preparing a medicament for preventing or treating melanoma.

In another embodiment of the present invention, the present invention may be a use of 6-(6-(6-methylpyridin-2-yl)-2,3-dihydro-1H-imidazo[1,2-a]imidazol-5-yl)-[1,2,4]triazol[1,5-a]pyridine or a pharmaceutically acceptable salt thereof, which is administered in combination with a CTLA-4 inhibitor (preferably an anti-CTLA-4 antibody or fragment thereof) for preparing a medicament for preventing or treating melanoma, colorectal cancer, sarcoma, breast cancer, cervical cancer, head and neck squamous cell carcinoma, or liver cancer.

In another embodiment of the present invention, the present invention may be a use of 6-(6-(6-methylpyridin-2-yl)-2,3-dihydro-1H-imidazo[1,2-a]imidazol-5-yl)-[1,2,4]triazole[1,5-a]pyridine or a pharmaceutically acceptable salt thereof, which is administered in combination with lenvatinib for preparing a medicament for preventing or treating colorectal cancer, cervical cancer, head and neck squamous cell carcinoma, or liver cancer.

In an embodiment of the present invention, the present invention may be a use of 6-(6-(6-methylpyridin-2-yl)-2,3-dihydro-1H-imidazo[1,2-a]imidazol-5-yl)-[1,2,4]triazol[1,5-a]pyridine or a pharmaceutically acceptable salt thereof, which is administered in combination with lenvatinib and a PD-1 inhibitor (preferably, an anti-PD-1 antibody or fragment thereof) for preparing a medicament for preventing or treating melanoma, colorectal cancer, head and neck squamous cell carcinoma, or liver cancer.

In another embodiment of the present invention, the present invention may be a use of 6-(6-(6-methylpyridin-2-yl)-2,3-dihydro-1H-imidazo[1,2-a]imidazol-5-yl)-[1,2,4]triazol[1,5-a]pyridine or a pharmaceutically acceptable salt thereof, which is administered in combination with lenvatinib and a CTLA-4 inhibitor (preferably an anti-CTLA-4 antibody or fragment thereof) for preparing a medicament for preventing or treating colorectal cancer, cervical cancer, head and neck squamous cell carcinoma, or liver cancer.

In an embodiment of the present invention, the present invention may be a use of 6-(6-(6-methylpyridin-2-yl)-2,3-dihydro-1H-imidazo[1,2-a]imidazol-5-yl)-[1,2,4]triazol[1,5-a]pyridine or a pharmaceutically acceptable salt thereof, which is administered in combination with a PD-1 inhibitor (preferably, an anti-PD-1 antibody or fragment thereof) and a CTLA-4 inhibitor (preferably, an anti-CTLA-4 antibody or fragment thereof) for preparing a medicament for preventing or treating colorectal cancer, cervical cancer, head and neck squamous cell carcinoma, or liver cancer.

Furthermore, the present invention may be a kit for preventing or treating a tumor, the kit including a low-molecular kinase inhibitor that blocks the signaling pathway of TGF-β, and an instruction manual that instruct the administration of a low-molecular kinase inhibitor that blocks the signaling pathway of TGF-β in combination with at least one selected from among an immune checkpoint regulator and a receptor tyrosine kinase inhibitor. In this case, the low-molecular kinase inhibitor that blocks the signaling pathway of TGF-β, the immune checkpoint regulator, and the receptor tyrosine kinase inhibitor may be administered simultaneously, sequentially, or separately, and the types of the low-molecular kinase inhibitor that blocks the signaling pathway of TGF-β, the immune checkpoint regulator, and the receptor tyrosine kinase inhibitor, the tumor types, the administration methods, and doses thereof are as defined above.

In an embodiment of the present invention, the present invention may be a kit for preventing or treating melanoma, colorectal cancer, bladder cancer, sarcoma, breast cancer, cervical cancer, head and neck squamous cell cancer, or liver cancer, the kit including: 6-(6-(6-methylpyridin-2-yl)-2,3-dihydro-1H-imidazo[1,2-a]imidazol-5-yl)-[1,2,4]triazole[1,5-a]pyridine or a pharmaceutically acceptable salt thereof; and an instruction manual that instruct the administration of 6-(6-(6-methylpyridin-2-yl)-2,3-dihydro-1H-imidazo[1,2-a]imidazol-5-yl)-[1,2,4]triazole[1,5-a]pyridine or a pharmaceutically acceptable salt thereof in combination with a PD-1 inhibitor (preferably, an anti-PD-1 antibody or fragment thereof).

In an embodiment of the present invention, the present invention may be a kit for preventing or treating melanoma, the kit including: 6-(6-(6-methylpyridin-2-yl)-2,3-dihydro-1H-imidazo[1,2-a]imidazol-5-yl)-[1,2,4]triazole[1,5-a]pyridine or a pharmaceutically acceptable salt thereof; and an instruction manual that instruct the administration of 6-(6-(6-methylpyridin-2-yl)-2,3-dihydro-1H-imidazo[1,2-a]imidazol-5-yl)-[1,2,4]triazole[1,5-a]pyridine or a pharmaceutically acceptable salt thereof in combination with a PD-L1 inhibitor (preferably, an anti-PD-L1 antibody or fragment thereof).

In another embodiment of the present invention, the present invention may be a kit for preventing or treating melanoma, colorectal cancer, sarcoma, breast cancer, cervical cancer, head and neck squamous cell cancer, or liver cancer, the kit including: 6-(6-(6-methylpyridin-2-yl)-2,3-dihydro-1H-imidazo[1,2-a]imidazol-5-yl)-[1,2,4]triazole[1,5-a]pyridine or a pharmaceutically acceptable salt thereof; and an instruction manual that instruct the administration of 6-(6-(6-methylpyridin-2-yl)-2,3-dihydro-1H-imidazo[1,2-a]imidazol-5-yl)-[1,2,4]triazole[1,5-a]pyridine or a pharmaceutically acceptable salt thereof in combination with a CTLA-4 inhibitor (preferably, an anti-CTLA-4 antibody or fragment thereof).

In another embodiment of the present invention, the present invention may be a kit for preventing or treating colorectal cancer, cervical cancer, head and neck squamous cell cancer, or liver cancer, the kit including: 6-(6-(6-methylpyridin-2-yl)-2,3-dihydro-1H-imidazo[1,2-a]imidazol-5-yl)-[1,2,4]triazole[1,5-a]pyridine or a pharmaceutically acceptable salt thereof; and an instruction manual that instruct the administration of 6-(6-(6-methylpyridin-2-yl)-2,3-dihydro-1H-imidazo[1,2-a]imidazol-5-yl)-[1,2,4]triazole[1,5-a]pyridine or a pharmaceutically acceptable salt thereof in combination with lenvatinib.

In an embodiment of the present invention, the present invention may be a kit for preventing or treating colorectal cancer, cervical cancer, head and neck squamous cell cancer, or liver cancer, the kit including: 6-(6-(6-methylpyridin-2-yl)-2,3-dihydro-1H-imidazo[1,2-a]imidazol-5-yl)-[1,2,4]triazole[1,5-a]pyridine or a pharmaceutically acceptable salt thereof; and an instruction manual that instruct the administration of 6-(6-(6-methylpyridin-2-yl)-2,3-dihydro-1H-imidazo[1,2-a]imidazol-5-yl)-[1,2,4]triazole[1,5-a]pyridine or a pharmaceutically acceptable salt thereof in combination with lenvatinib and a PD-1 inhibitor (preferably, an anti-PD-1 antibody or fragment thereof).

In another embodiment of the present invention, the present invention may be a kit for preventing or treating colorectal cancer, cervical cancer, head and neck squamous cell cancer, or liver cancer, the kit including: 6-(6-(6-methylpyridin-2-yl)-2,3-dihydro-1H-imidazo[1,2-a]imidazol-5-yl)-[1,2,4]triazole[1,5-a]pyridine or a pharmaceutically acceptable salt thereof; and an instruction manual that instruct the administration of 6-(6-(6-methylpyridin-2-yl)-2,3-dihydro-1H-imidazo[1,2-a]imidazol-5-yl)-[1,2,4]triazole[1,5-a]pyridine or a pharmaceutically acceptable salt thereof in combination with lenvatinib and a CTLA-4 inhibitor (preferably, an anti-CTLA-4 antibody or fragment thereof).

In an embodiment of the present invention, the present invention may be a kit for preventing or treating colorectal cancer, cervical cancer, head and neck squamous cell cancer, or liver cancer, the kit including: 6-(6-(6-methylpyridin-2-yl)-2,3-dihydro-1H-imidazo[1,2-a]imidazol-5-yl)-[1,2,4]triazole[1,5-a]pyridine or a pharmaceutically acceptable salt thereof; and an instruction manual that instruct the administration of 6-(6-(6-methylpyridin-2-yl)-2,3-dihydro-1H-imidazo[1,2-a]imidazol-5-yl)-[1,2,4]triazole[1,5-a]pyridine or a pharmaceutically acceptable salt thereof in combination with a PD-1 inhibitor (preferably, an anti-PD-1 antibody or fragment thereof) and a CTLA-4 inhibitor (preferably, an anti-CTLA-4 antibody or fragment thereof).

MODES FOR THE INVENTION

Examples

Hereinafter, the present invention will be described in more detail with reference to the following examples. However, in the following examples, in order to illustrate the present invention, Compound 1 (6-(6-(6-methylpyridine-2-yl)-2,3-dihydro-1H-imidazo[1,2-a]imidazol-5-yl)-[1,2,4]triazole[1,5-a]pyridine phosphate) was used as a low-molecular kinase inhibitor that blocks the signaling pathway of TGF-β, or a pharmaceutically acceptable salt thereof, but the scope of the present invention is not limited to the corresponding compound.

Example 1. Anti-Tumor Effects in Melanoma Mouse Model

Example 1.1. Combination of Anti-PD-1 Antibody and Compound 1

Example 1.1.1. Preparation of Melanoma Mouse Model and Study Drug 40 female C57BL/6 mice, which were 6-8 weeks old, were purchased from OrientBio, and $1\times10^6$ B16F10 cell lines (KCLB, #80008) were subcutaneously injected into the right flank of each mouse, thereby transplanting the cancer cell lines thereto.

The B16F10 cell line transplantation date was determined as Day 0, and the tumor volume was measured on Day 9. The mice were classified according to the mean and deviation of the tumor volume on Day 9.

A 0.9% physiological saline solution was prepared as a vehicle, and a mixed solution of a mouse anti-PD-1 antibody (BioXCell, clone #RMP1-14) and PBS, and a mixed solution of Compound 1 and the vehicle were prepared.

Example 1.1.2. Method for Administration, Measurement Variables, and Statistical Analysis of Study Drugs The mice classified in Example 1.1.1. were assigned to a control group (vehicle oral administration), a group in which Compound 1 was orally administered, a group in which an anti-PD-1 antibody was intraperitoneally administered, or a group in which an anti-PD-1 antibody was administered in combination with Compound 1, and drug administration was initiated on Day 9 from the B16F10 cell line transplantation date, and the study was terminated on Day 24 from the drug administration date. The dose and administration method of the drug administered to each group are shown in Table 1 below, and when administered orally (p.o) and intraperitoneally (i.p.), the dose per individual is 5 mL/kg in the both cases.

TABLE 1

| Drug | Number of mice |
|---|---|
| Vehicle twice a day (p.o.) | 10 |
| Compound 1, 50 mg/kg, twice a day (p.o.) | 10 |
| Mouse anti-PD-1 antibody, 10 mg/kg, once every three days (i.p.) | 10 |
| Mouse anti-PD-1 antibody, 10 mg/kg, once every three days (i.p.) + Compound 1, 50 mg/kg, twice a day (p.o.) | 10 |

The mouse tumor volume and weight were measured twice a week during the study period after the drug administration. The mouse tumor volume was calculated as (tumor length (L)×tumor width (W)×tumor width (W))÷2, wherein the tumor length (L) is the longest tumor dimension, and the tumor width (W) is the longest tumor dimension perpendicular to L. Meanwhile, when the tumor volume of an individual mouse was greater than 3,000 $mm^3$, the corresponding mouse was euthanized and the study was terminated.

A change in tumor volume for each group was statistically analyzed using Two-way ANOVA test.

Example 1.1.3. Tumor Growth Inhibitory Effect and Weight Change

When comparing the tumor volume measured on Day 15 from the drug administration date, it was found that the tumor volume of a group in which an anti-PD-1 antibody was administered alone was 45% lower than the tumor volume measured in the control group, the tumor volume of a group in which Compound 1 was administered alone was 44% lower than the tumor volume measured in the control group, whereas the tumor volume of the combined administration group of the anti-PD-1 antibody and Compound 1 was 74% lower than the tumor volume measured in the control group. In addition, when the tumor volume on Day 15 from the drug administration was examined, it was found that the tumor volume of the group in which Compound 1 was administered in combination with the anti-PD-1 antibody had a statistically significant level of difference (i.e., $p<0.05$ and $p<0.001$) compared to the group in which the anti-PD-1 antibody was administered alone or the group in which Compound 1 was administered alone (see FIG. 1).

There was no statistically significant difference in weight changes between the control group and the drug administration group during the entire study period (see FIG. 2).

Example 1.2. Combination of Anti-PD-L1 Antibody and Compound 1

Example 1.2.1. Preparation of Melanoma Mouse Model and Study Drug 90 female C57BL/6 mice, which were 8 weeks old, were purchased from OrientBio, and a melanoma mouse model was prepared by the method used in the preparation of the melanoma mouse model in Example 1.1.1. The B16F10 cell line transplantation date was determined as Day 0, and the tumor volume was measured on Day 4. The mice were classified according to the mean and deviation of the tumor volume on Day 4.

The vehicle used in Example 1.1.1 and PBS were used as carriers to prepare a mixed solution of a mouse anti-IgG2b antibody (BioXCell) and PBS, a mixed solution of a mouse anti-PDL1 antibody (BioXCell) and PBS, a mixed solution of Compound 1 and the vehicle, and a mixed solution of LY2157299 (Chembo Pharma) and the vehicle.

Example 1.2.2. Method for Administration, Measurement Variables, and Statistical Analysis of Study Drug The mice classified in Example 1.2.1 were assigned to a control group (combined administration of vehicle and an anti-IgG2b antibody and PBS mixture), a vehicle and anti-PDL1 antibody administration group, a combined administration group of anti-PDL1 antibody and Compound 1 (low dose: 15 mg/kg/day, high dose: 30 mg/kg/day), or a combined administration group of anti-PDL1 antibody and LY2157299 (low dose: 75 mg/kg/day, high dose: 150 mg/kg/day), and drugs were administered from Day 4 to Day 21 from the date of B16F10 cell line transplantation, and the study was terminated on Day 22. The dose and administration method of the drug administered to each group are shown in Table 2 below, and when administered orally (p.o) and intraperitoneally (i.p.), the dose per individual was 10 mL/kg in the both cases.

TABLE 2

| Drug | Number of mice |
|---|---|
| Vehicle, twice a day (p.o.) + 12.5 mg/kg, Mouse anti-IgG2b antibody, twice a week (i.p.) | 15 |
| Vehicle, twice a day (p.o.) + Mouse anti-PD-L1 antibody, 12.5 mg/kg, twice a week (i.p.) | 15 |
| Mouse anti-PD-L1 antibody, 12.5 mg/kg, twice a week (i.p.) + Compound 1* 15 mg/kg/day, twice a day (p.o., 7.5 mg/kg/time) * the amount is calculated with the salt included | 15 |
| Mouse anti-PD-L1 antibody, 12.5 mg/kg, twice a week (i.p.) + Compound 1* 30 mg/kg/day, twice a day (p.o., 15 mg/kg/time) * the amount is calculated with the salt included | 15 |
| Mouse anti-PD-L1 antibody, 12.5 mg/kg, twice a week (i.p.) + LY2157299 75 mg/kg/day, twice a day (p.o., 37.5 mg/kg/time) | 15 |
| Mouse anti-PD-L1 antibody, 12.5 mg/kg, twice a week (i.p.) + LY2157299 150 mg/kg/day, twice a day (p.o., 75 mg/kg/time) | 15 |

The tumor volume of mice was measured at intervals of 2 days from the date of drug administration, and the tumor volume was measured by autopsy at the end of the study. In this case, the mouse tumor volume was calculated by the same method as the tumor volume calculation method of Example 1.1.2. In addition, mouse weights were measured on Day 4, Day 7, Day 11, Day 14, Day 18 and Day 21 from the date of B16F10 cell line transplantation. Tumor volume changes and weight changes for each group were statistically analyzed using Tukey's multiple comparison after ANOVA test. When comparing tumor volumes on Day 22 from the date of B16F10 cell line transplantation, statistical significance compared to the control group in which a vehicle and anti-IgG2b antibody were administered was analyzed using Dunnett's multiple comparison after ANOVA test. The statistical significance between the group in which the mouse anti-PD-L1 antibody, the study drug, was administered alone and the group in which Compound 1 was administered in combination with the anti-PD-L1 antibody on Day 22 from the date of the B16F10 cell line transplantation was analyzed by Student's t-test.

Example 1.2.3. Tumor Growth Inhibitory Effect and Weight Change

Except the group in which low-dose LY2157299 was administered in combination with an anti-PD-L1 antibody, the group in which an anti-PD-L1 antibody was administered alone, the low-dose compound 1 and anti-PD-L1 antibody combination administration group, the group in which high-dose Compound 1 was administered in combination with an anti-PD-L1 antibody, and the group in which high-dose LY2157299 was administered in combination with an anti-PD-L1 antibody were found to have a significant tumor growth inhibitory effect compared to the control group from Day 7 of drug administration (i.e., Day from the B16F10 cell line transplantation date) to Day 19 (Day 22 from the cell line transplantation date) (see FIG. 3). Specifically, when the difference from the tumor volume of the control group was statistically analyzed using ANOVA test and Tukey's multiple comparison, it was found that the difference was statistically significant (*: $p<0.05$; : $p<0.01$; *: $p<0.001$).

In particular, on Day 22 from the B16F10 cell line transplantation date, which was the end of the study, only the group in which high-dose Compound 1 was administered in combination with the anti-PD-L1 antibody showed a statistically significant decrease (*, $p<0.05$) in tumor volume compared to the control group (see FIG. 4), and also showed a statistically significant decrease (#, $p<0.05$, one-tailed Student's t-test) compared to the group in which the anti-PD-L1 antibody was administered alone (see FIGS. 3 and 4). There was no statistically significant difference in weight changes between the control group and the drug administration group during the entire study period (see FIG. 5).

Example 1.3. Combined Administration of Anti-CTLA-4 Antibody and Compound 1

Example 1.3.1. Preparation of Melanoma Mouse Model and Study Drug 40 female C57BL/6 mice, which were 6-8 weeks old, were purchased from OrientBio, and $1\times10^6$ B16F10 cell lines (KCLB, #80008) were subcutaneously injected into the right flank of each mouse, thereby transplanting the cancer cell lines thereto.

The B16F10 cell line transplantation date was determined as Day 0, and the tumor volume was measured on Day 9. The mice were classified according to the mean and deviation of the tumor volume on Day 9.

A 0.9% physiological saline solution was prepared as a vehicle, and a mixed solution of a mouse anti-CTLA-4 antibody (BioXCell, clone #9D9) and PBS, and a mixed solution of Compound 1 and the vehicle were prepared as the study drug.

Example 1.3.2. Method for Administration, Measurement Variables, and Statistical Analysis of Study Drug The mice classified in Example 1.3.1 were assigned to a control group (vehicle oral administration), a Compound 1 oral administration group, an anti-CTLA-4 antibody intraperitoneal administration group, or a combined administration group of an anti-CTLA-4 antibody and Compound 1, and drug administration was initiated from Day 9 to Day 21 from the B16F10 cell line transplantation date, and the study was terminated on Day 22. The dose and administration method of the drug administered to each group are shown in Table 3 below, and when administered orally (p.o) and intraperitoneally (i.p.), the dose per individual is 5 mL/kg in the both cases.

TABLE 3

| Drug | Number of mice |
|---|---|
| Vehicle, twice a day (p.o.) | 10 |
| Compound 1, 50 mg/kg, twice a day (p.o.) | 10 |
| Mouse anti-CTLA-4 antibody, 10 mg/kg, once every three days (i.p.) | 10 |
| Mouse anti-CTLA-4 antibody, 10 mg/kg, once every three days (i.p.) + Compound 1, 50 mg/kg, twice a day (p.o.) | 10 |

The mouse tumor volume and weight were measured twice a week during the study period after the drug administration. In this case, the mouse tumor volume was calculated by the same method as the tumor volume calculation method of Example 1.1.2. Meanwhile, when the tumor volume of an individual mouse was greater than 3,000 $mm^3$, the corresponding mouse was euthanized and the study was terminated.

Tumor volume changes and weight changes for each group were statistically analyzed using Two-way ANOVA test and one-tailed t-test.

Example 1.3.3. Tumor Growth Inhibitory Effect and Weight Change

During the drug administration period, it was found that the group in which Compound 1 was administered in combination with the anti-CTLA-4 antibody had a difference in an excellent tumor growth inhibitory effect compared to the vehicle administration group, the group in which Compound 1 was administered alone, or the group in which the anti-CTLA-4 antibody was administered alone (see FIG. 6A).

In addition, when the tumor volume on Day 15 from the drug administration was examined, it was found that the tumor volume of the group in which Compound 1 was administered in combination with the anti-CTLA-4 antibody had a statistically significant level of difference (i.e., $p<0.01$) compared to the group in which the anti-CTLA-4 antibody was administered alone or the group in which Compound 1 was administered alone (see FIG. 6B).

There was no statistically significant difference in weight changes between the control group and the drug administration group during the entire study period (see FIG. 7).

Example 2. Anti-Tumor Effects in Colorectal Cancer Mouse Model

Example 2.1. Preparation of Colorectal Cancer Mouse Model and Study Drug 170 female BALB/C mice, which were 6-8 weeks old, were purchased from OrientBio, and cancer cell lines were transplanted by subcutaneously injecting $7.5\times10^5$ CT26 cell lines (Murine colon cancer cells) into the right flank of each mouse. The CT26 cell line transplantation date was determined as Day 0, and the tumor volume was measured on Day 7. The average tumor volume on Day 7 was found to be 50 $mm^3$, and 110 mice were selected except individuals of which the tumor volume was significantly larger or smaller than the average tumor volume.

A 0.9% physiological saline solution was prepared as a vehicle, and a mixed solution of a mouse anti-PD-1 antibody (BioXCell, clone #RMP1-14) and PBS, a mixed solution of a mouse anti-CTLA-4 antibody (BioXCell, clone #9D9) and PBS, a mixed solution of lenvatinib and the vehicle, and a mixed solution of Compound 1 and the vehicle were prepared.

Example 2.2. Method for Administration, Measurement Variables, and Statistical Analysis of Study Drug The mice selected in Example 2.1 were assigned to the groups listed in Table 4 below, and vehicles or drugs were administered, and drug administration was initiated on Day 7 from the cell line inoculation date, and the study was terminated on Day 27 from the drug administration date.

TABLE 4

| Drug | Number of mice |
|---|---|
| Vehicle twice a day (p.o.) | 10 |
| Mouse anti-PD-1 antibody, 10 mg/kg, once every three days (i.p.) | 10 |
| Compound 1, 50 mg/kg, twice a day (p.o.) | 10 |
| Mouse anti-CTLA-4 antibody, 3 mg/kg, once every three days (i.p.) | 10 |
| Mouse anti-CTLA-4 antibody, 10 mg/kg, once every three days (i.p.) | 10 |
| Lenvatinib, 10 mg/kg, once a day (p.o.) | 10 |
| Mouse anti-PD-1 antibody, 10 mg/kg, once every three days (i.p.) + Compound 1, 50 mg/kg, twice a day (p.o.) | 10 |
| Mouse anti-CTLA-4 antibody, 3 mg/kg, once every three days (i.p.) + Compound 1, 50 mg/kg, twice a day (p.o.) | 10 |
| Mouse anti-CTLA-4 antibody, 10 mg/kg, once every three days (i.p.) + Compound 1, 50 mg/kg, twice a day (p.o.) | 10 |
| Mouse anti-PD-1 antibody, 10 mg/kg, once every three days (i.p.) + Mouse anti-CTLA-4 antibody, 10 mg/kg, once every three days (i.p.) | 10 |
| Lenvatinib, 10 mg/kg, once a day (p.o.) + Compound 1, 50 mg/kg, twice a day (p.o.) | 10 |
| Mouse anti-CTLA-4 antibody, 3 mg/kg, once every three days (i.p.) + Lenvatinib, 10 mg/kg, twice a day (p.o.) | 10 |
| Mouse anti-PD-1 antibody, 10 mg/kg, once every three days (i.p.) + Lenvatinib, 10 mg/kg, twice a day (p.o.) | 10 |
| Mouse anti-PD-1 antibody, 10 mg/kg, once every three days (i.p.) + Mouse anti-CTLA-4 antibody, 3 mg/kg, once every three days (i.p.) + Compound 1, 50 mg/kg, twice a day (p.o.) | 10 |
| Mouse anti-PD-1 antibody, 10 mg/kg, once every three days (i.p.) + Mouse anti-CTLA-4 antibody, 10 mg/kg, once every three days (i.p.) + Compound 1, 50 mg/kg, twice a day (p.o.) | 10 |
| Lenvatinib, 10 mg/kg, once a day (p.o.) + Mouse anti-CTLA-4 antibody, 3 mg/kg, once every three days (i.p.) + Compound 1, 50 mg/kg, twice a day (p.o.) | 10 |
| Lenvatinib, 10 mg/kg, once a day (p.o.) + Mouse anti-PD-1 antibody, 10 mg/kg, once every three days (i.p.) + Compound 1, 50 mg/kg, twice a day (p.o.) | 10 |

When administered orally (p.o) and intraperitoneally (i.p.), the dose was 5 mL/kg in the both cases.

The mouse tumor volume and weight were measured twice a week during the study period after the drug administration. In this case, the mouse tumor volume was calculated by the same method as the tumor volume calculation method of Example 1.1.2. Meanwhile, when the tumor volume of an individual mouse was greater than 3,000 $mm^3$, the corresponding mouse was euthanized and the study was terminated.

Tumor volume changes and weight changes for each group were statistically analyzed using Two-way ANOVA test, Bonferroni test, and one-tailed t-test.

Example 2.3. Tumor Growth Inhibitory Effects

Example 2.3.1. Combination Administration of Compound 1 and Anti-PD-1 Antibody and Combination of Compound 1 and Anti-CTLA-4 Antibody The tumor volume of the group in which the anti-PD-1 antibody was administered in combination with Compound 1 was measured to be lower than that of the group in which the anti-PD-1 antibody was administered alone, the group in which Compound 1 was administered alone, or the control group in which the vehicle was administered (see FIG. 8A). In addition, when comparing the tumor volume measured on Day 26 from the drug administration date, it was found that the tumor volume of a group in which an anti-PD-1 antibody was administered alone was 4.8% lower than the tumor volume measured in the control group, the tumor volume of a group in which Compound 1 was administered alone was 59% lower than the tumor volume measured in the control group, whereas the tumor volume of the combined administration group of the anti-PD-1 antibody and Compound 1 was 77% lower than the tumor volume measured in the control group. Furthermore, when the tumor weight (g) measured on Day 26 from the drug administration date was compared, it was found that the tumor weight of the group in which the anti-PD-1 antibody was in combination with Compound 1 was the smallest, and the difference in the tumor weights of the group in which Compound 1 was administered alone, and the group in which the anti-PD-1 antibody was administered in combination with Compound 1 was found to be statistically significant (see FIG. 8B).

In addition, the tumor volume of the group in which the high-dose anti-CTLA antibody was administered in combination with Compound 1 was measured to be lower than the tumor volume of the group in which the high-dose anti-CTLA antibody was administered alone, the group in which Compound 1 was administered alone, or the control group in which only the vehicle was administered over the entire study period (see FIG. 9A). In addition, when the tumor volume measured on Day 26 from the drug administration date was compared, it was found that the tumor volume of the group in which the high-dose anti-CTLA-4 antibody was administered alone was lower by 27% than the tumor volume of the control group, the tumor volume of the group in which Compound 1 was administered alone was lower by 59% than the tumor volume of the control group, and the tumor volume of the group in which the high-dose anti-CTLA-4 antibody was administered in combination with Compound 1 was lower by 77% than the tumor volume of the control group (see FIG. 9B).

Moreover, the tumor volume observed in the group in which the anti-PD-1 antibody, the low-dose anti-CTLA-4 antibody, and Compound 1 were administered in combination was found to be lower than the tumor volume observed in the group in which only the vehicle was administered alone, the group in which the anti-PD-1 antibody was administered alone, the group in which the low-dose anti-CTLA-4 antibody was administered alone, the group in which Compound 1 was administered alone, the group in which the anti-PD-1 antibody was administered in combination with the high-dose anti-CTLA-4 antibody, and the group in which Compound 1 was administered in combination with the low-dose anti-CTLA-4 antibody (see FIG. 10). In addition, the tumor volume of the group in which the anti-PD-1 antibody, the low-dose anti-CTLA-4 antibody, and Compound 1 were administered in combination was lower by 88% than the tumor volume of the control group in which only the vehicle was administered, and the tumor volumes observed in the group in which the anti-PD-1 antibody was administered alone, the group in which the low-dose anti-CTLA-4 antibody was administered alone, the group in which Compound 1 was administered alone, the group in which Compound 1 was administered in combination with the low-dose anti-CTLA-4 antibody, and the group in which the anti-PD-1 antibody was administered in combination with the high-dose anti-CTLA-4 antibody was lower by 4.8%, 23%, 59%, 60%, and 63% than the tumor volume of the control group in which only the vehicle was administered, respectively (see FIG. 10).

Example 2.3.2. Combination of Compound 1 and Lenvatinib or Combination of Compound 1 and Lenvatinib and Anti-PD-1 Antibody and/or Anti-CTLA-4 Antibody The tumor volume of the group in which lenvatinib was administered in combination with Compound 1 was measured to be lower than the tumor volume of the group in which the anti-PD-1 antibody was administered alone, the group in which lenvatinib was administered alone, the group in which Compound 1 was administered alone, the group in which lenvatinib was administered in combination with the anti-PD-1 antibody, or the control group in which only the vehicle was administered over the entire study period, and the tumor volume in which lenvatinib, Compound 1, and the anti-PD-1 antibody were administered in combination was found to be lower than the tumor volume of the group in which lenvatinib was administered in combination with Compound 1 (see FIG. 11). In addition, the tumor volume of the group in which lenvatinib, the anti-CTLA-4 antibody, and Compound 1 were administered in combination was measured to be lower than the tumor volume of each of the group in which the anti-CTLA-4 antibody was administered alone, the group in which lenvatinib was administered alone, the group in which lenvatinib was administered in combination with the anti-PD-1 antibody, the group in which lenvatinib was administered in combination with the anti-CTLA-4 antibody, and the control group over the entire study period (see FIG. 12).

Furthermore, when the tumor volume measured on Day 26 from the drug administration date was compared, the drops in the tumor volume of the group in which Compound 1 was administered alone, the group in which lenvatinib was administered alone, the group in which the anti-PD-1 antibody was administered alone, the group in which the anti-CTLA-4 antibody was administered alone, the group in which lenvatinib was administered in combination with the anti-PD1 antibody, and the group in which lenvatinib was administered in combination with the anti-CTLA-4 antibody were 59%, 30%, 4.8%, 23%, 41%, and 56%, respectively, as compared to the tumor volume of the control group in which only the vehicle was administered.

On the other hand, when the tumor volume measured on Day 26 from the drug administration date was compared, the drops in the tumor volume of the group in which lenvatinib was administered in combination with Compound 1 and the group in which lenvatinib, Compound 1, and the anti-PD-1 antibody were administered in combination were found to be 68% and 90%, respectively, as compared to the tumor volume of the control group in which only the vehicle was administered. In addition, the drop in the tumor volume of the group in which lenvatinib, Compound 1, and the anti-CTLA-4 antibody were administered in combination was 82% as compared to the tumor volume of the control group in which only the vehicle was administered.

In summary, it is confirmed that using Compound 1 in combination with at least one selected from among lenvatinib, the anti-PD-1 antibody, and the anti-CTLA-4 antibody shows an anti-cancer effect superior to that of the case of using lenvatinib, the anti-PD-1 antibody, or the anti-CTLA-4 antibody alone or administering the vehicle only.

Example 2.4. Weight Changes

There was no statistically significant difference in weight changes between the drug administration group and the control group in which only the vehicle was administered during the entire study period (see FIG. 13).

Example 2.5. In Vitro Test for Confirming Whether Compound 1 and Lenvatinib Overlap in Mechanism of Action To confirm whether Compound 1 and lenvatinib overlap in the mechanism of action, recovery of the inhibited IFN-γ secretion function of T cells was measured under the condition of T cell receptor single stimulus. Changes in IFN-γ secretion in hPBMCs were measured by treating human peripheral blood mononuclear cells (hPBMCs) only with vehicle, treating only anti-CD3 antibodies and anti-CD28 antibodies (T cell stimulants), treating only TGF-β (T cell function inhibitors), or treating lenvatinib and/or Compound 1 with TGF-β, anti-CD3 antibodies, and anti-CD28 antibodies.

First, under the conditions of 37° C., 5% carbon dioxide humidification incubator, human peripheral blood mononuclear cells (hPBMCs) were cultured in RPMI-1640 medium supplemented with 10% heat-inactivated FBS, 2 mM L-glutamine, 1 mM sodium pyruvate, 10 mM HEPES, and 1×NEAA.

A 6-well plate was coated with anti-CD3 monoclonal antibodies (OKT3) at 4° C. overnight. Each well of the 6-well plate was suctioned with an antibody solution, and washed using PBS. hPBMCs were plated on the coated 6-well plate. In order to increase the reactivity of hPBMCs, culturing was performed for 5 days under the conditions of 37° C., 5% carbon dioxide humidification incubator. The hPBMCs cultured for 5 days were inoculated in a 96-well plate at a concentration of $1\times10^5$ cells/well. The hPBMCs inoculated in the 96-well plate were treated with lenvatinib or Compound 1 and the hPBMCs were incubated for 1 hour, then TGF-β was added thereto and the hPBMCs were cultured for 1 hour. The hPBMCs were treated with anti-CD3 antibody/anti-CD28 antibody-coated microbeads so that the ratio of cell:beads was 2:1 and the hPBMCs were stimulated for 72 hours. After 72 hours, the supernatants were recovered and conventional IFN-γ ELISA was performed. The IFN-γ content generated for each group was measured. Data analysis was performed using Prism 5 (GraphPad Software, Inc.), and statistical analysis was performed using One-way ANOVA and Tukey's multiple comparison.

As a result of ELISA analysis, the stimulus with anti-CD3 antibodies and anti-CD28 antibodies increased the secretion of IFNγ in human PBMCs, and TGF-3 treatment inhibited the secretion of IFNγ in human PBMCs. In addition, treatment of lenvatinib with anti-CD3 antibodies, anti-CD28 antibodies, and TGF-β resulted in increased secretion of IFNγ in human PBMCs, and treatment of Compound 1 with anti-CD3 antibodies, anti-CD28 antibodies and TGF-β resulted in increased secretion of IFNγ in human PBMCs. Furthermore, treatment of Compound 1 and lenvatinib with anti-CD3 antibodies, anti-CD28 antibodies, and TGF-β was shown to increase the secretion of IFNγ, similar to the stimulus with anti-CD3 antibodies and anti-CD28 antibodies. Therefore, it was confirmed that the mechanism of action of the two drugs acts independently.

Meanwhile, lenvatinib is known to have insufficient anticancer effects in an endothelial cell anergy environment accompanied by a decrease in binding proteins such as VCAM-1 generated on the surface of vascular endothelial cells. Therefore, using Compound 1 in combination with lenvatinib having different mechanism of action complements and improves the anti-cancer effect of lenvatinib.

Example 3. Anti-Tumor Effects in Sarcoma Mouse Model

Example 3.1. Preparation of Sarcoma Mouse Models and Study Drugs 60 female BALB/C mice, 6-8 weeks old, were purchased from Vital River Laboratories Research Model and Services Company. $1\times10^6$ WEHI-164 cell lines (Murine sarcoma cells) were injected subcutaneously into the right flank of each mouse to transplant a cancer cell line. The WEHI-164 cell line transplantation date was determined as Day 0, and the tumor volume was measured on Day 7. The average tumor volume on Day 7 was found to be 53 mm, and mice were selected to maintain a constant average and deviation for each group by excluding individuals having a significantly larger tumor volume or a significantly smaller tumor volume than the average tumor volume.

A 0.9% physiological saline solution was prepared as a vehicle, and a mixed solution of an anti-PD-1 antibody (BioXCell) and PBS, a mixed solution of an anti-CTLA-4 antibody (BioXCell) and PBS, and a mixed solution of Compound 1 and the vehicle were prepared as study drugs.

Example 3.2. Method for Administration, Measurement Variables, and Statistical Analysis of Study Drugs The mice selected in Example 3.1 were assigned to a control group, a group in which an anti-PD-1 antibody was administered, a group in which Compound 1 was administered, a group in which an anti-CTLA-4 antibody was administered, a group in which Compound 1 was administered in combination with an anti-PD-1 antibody, or a group in which Compound 1 was administered in combination with an anti-CTLA-4 antibody, respectively. Drugs were administered from Day 7 to Day 23 from the WEHI-164 cell line transplantation date. The dose and administration method of the drug administered to each group are shown in Table 5 below, and when administered orally (p.o) and intraperitoneally (i.p.), the dose was 5 mL/kg in the both cases.

TABLE 5

| Drug | Number of mice |
|---|---|
| Vehicle twice a day (p.o) | 10 |
| Mouse anti-PD-1 antibody, 10 mg/kg, once a week (i.p.) | 10 |
| Compound 1, 50 mg/kg, twice a day (p.o.) | 10 |
| Mouse anti-CTLA-4 antibody, 10 mg/kg, once a week (i.p.) | 10 |
| Mouse anti-PD-1 antibody, 10 mg/kg, once a week (i.p.) + Compound 1, 50 mg/kg, twice a day (p.o.) | 10 |
| Mouse anti-CTLA-4 antibody, 10 mg/kg, once a week (i.p.) + Compound 1, 50 mg/kg, twice a day (p.o.) | 10 |

Changes in tumor volumes and weights of mice during the study period after drug administration were measured twice a week, and the tumor volumes were measured by the same method as the method for measuring the tumor volumes in Example 1.1.2. Meanwhile, when the tumor volume of an individual mouse was greater than 3,000 $mm^3$, the corresponding mouse was euthanized and the study was terminated.

The difference in tumor volumes during the study period was statistically analyzed using one-tailed t-test, ANOVA and Tukey's multiple comparison test.

Example 3.3. Tumor Growth Inhibitory Effect and Remission Rate

The tumor volume of the group in which the anti-PD-1 antibody was administered in combination with Compound 1 was shown to be smaller than that of the group in which the anti-PD-1 antibody was administered alone, the group in which Compound 1 was administered alone, or the control group in which the vehicle was administered (see FIG. 14). In addition, the tumor volume of the group in which the anti-PD-1 antibody was administered alone measured on Day 16 from the drug administration initiation date was smaller by 64% than the tumor volume of the control group, and the tumor volume of the group in which Compound 1 was administered alone was smaller by 71% than the tumor volume of the control group. However, it was found that the tumor volume of the group in which the anti-PD-1 antibody was administered in combination with Compound 1 was smaller by a staggering 98% than the tumor volume of the control group, and a difference in the tumor volume between the group in which the anti-PD-1 antibody was administered in combination with Compound 1 and the group in which Compound 1 was administered alone or the group in which the anti-PD-1 antibody was administered alone was statistically significant ($p<0.05$) (see FIG. 14).

In addition, it was observed that the complete remission rate of the tumor when the anti-CTLA-4 antibody was administered alone compared to the control group in which the vehicle was administered was 20%, the complete remission rate of the tumor when Compound 1 was administered alone compared to the control group in which the vehicle was administered was 30%, and the complete remission rate of the tumor when the anti-CTLA-4 antibody was administered in combination with Compound 1 compared to the control group in which the vehicle was administered was 80%. The difference in the complete remission rate of the tumor between the group in which the anti-CTLA-4 antibody was administered in combination with Compound 1 and the group in which the anti-CTLA-4 antibody was administered alone or the group in which Compound 1 was administered alone was statistically significant ($p<0.05$), and thus the combination administration of the anti-CTLA-4 antibody and Compound 1 has an excellent effect of suppressing tumor growth (see FIG. 15).

There was no statistically significant difference in weight changes between the drug administration group and the control group in which only the vehicle was administered during the entire study period (see FIG. 16).

Example 4. Anti-Tumor Effects in Breast Cancer Mouse Model

Example 4.1. Preparation of Breast Cancer Mouse Model and Study Drug 60 female BALB/C mice, 6-8 weeks old, were purchased from Vital River Laboratories Research Model and Services Company. $3\times10^5$ 4T1 cell lines (Murine breast cancer cells) were injected subcutaneously into the right flank of each mouse to transplant a cancer cell line. The 4T1 cell line transplantation date was determined as Day 0, and the tumor volume was measured on Day 6. The average tumor volume on Day 6 was found to be 52 $mm^3$, and mice were selected to maintain a constant average and deviation for each group by excluding individuals having a significantly larger tumor volume or a significantly smaller tumor volume than the average tumor size.

A 0.9% physiological saline solution was prepared as a vehicle, and a mixed solution of an anti-PD-1 antibody (BioXCell) and PBS, a mixed solution of an anti-CTLA-4 antibody (BioXCell) and PBS, and a mixed solution of Compound 1 and the vehicle were prepared as study drugs.

Example 4.2. Method for Administration, Measurement Variables, and Statistical Analysis of Study Drugs The mice selected in Example 4.1 were assigned to a control group, a group in which an anti-PD-1 antibody was administered, a group in which Compound 1 was administered, a group in which an anti-CTLA-4 antibody was administered, a group in which Compound 1 was administered in combination with an anti-PD-1 antibody, or a group in which Compound 1 was administered in combination with an anti-CTLA-4 antibody, respectively. Drugs were administered from Day 6 to Day 30 from the 4T1 cell line transplantation date. The dose and administration method of the drug administered to each group are shown in Table 6 below, and when administered orally (p.o) and intraperitoneally (i.p.), the dose was 5 mL/kg in the both cases.

TABLE 6

| Drug | Number of mice |
|---|---|
| Vehicle, twice a day (p.o.) | 10 |
| Mouse anti-PD-1 antibody, 10 mg/kg, dosing every three days (i.p.) | 10 |
| Compound 1, 50 mg/kg, twice a day (p.o.) | 10 |
| Mouse anti-CTLA-4 antibody, 10 mg/kg, dosing every three days (i.p.) | 10 |
| Mouse anti-PD-1 antibody, 10 mg/kg, dosing every three days (i.p.) + Compound 1, 50 mg/kg, twice a day (p.o.) | 10 |
| Mouse anti-CTLA-4 antibody, 10 mg/kg, dosing every three days (i.p.) + Compound 1, 50 mg/kg, twice a day (p.o.) | 10 |

Changes in tumor volumes and weights of mice during the study period after drug administration were measured twice a week, and the tumor volumes were measured by the same method as the method for measuring the tumor volumes in Example 1.1.2. Meanwhile, when the tumor volume of an individual mouse was greater than 3,000 $mm^3$, the corresponding mouse was euthanized and the study was terminated.

The difference in tumor volumes was statistically analyzed using ANOVA and Tukey's multiple comparison test.

Example 4.3. Tumor Growth Inhibitory Effect and Remission Rate

The tumor volume of the group in which the anti-PD-1 antibody was administered in combination with Compound 1 was shown to be smaller than that of the group in which the anti-PD-1 antibody was administered alone, the group in which Compound 1 was administered alone, or the control group in which the vehicle was administered (see FIG. 17A). In addition, the tumor volume of the group in which the anti-PD-1 antibody was administered alone measured on Day 23 from the cell line inoculation date was increased by 2.6% compared to the tumor volume of the control group, and the tumor volume in which Compound 1 was administered alone was reduced by 16% compared to the tumor volume of the control group (see FIG. 17B) On the other hand, the tumor volume of the group in which the anti-PD-1 antibody was administered in combination with Compound 1 was found to be reduced by a staggering 35% compared to the tumor volume of the control group, and a difference in the tumor volume between the control group and the group in which the anti-PD-1 antibody was administered in combination with Compound 1 was found to be less than 0.001 of a p-value when analyzed by using two-way ANOVA, and was found to be less than 0.01 of a p-value when analyzed by using one-way ANOVA and Tukey's multiple comparison test, resulting in a statistically significant decrease in the tumor volume compared to the control group (see FIGS. 17A-17B).

In addition, compared to the tumor volume of the control group in which the vehicle was administered measured on Day 23 from the cell line inoculation date, the tumor volume when the anti-CTLA-4 antibody was administered alone was decreased by 17%, and the tumor volume when Compound 1 was administered alone was decreased by 16% compared to the tumor volume of the control group in which the vehicle was administered, whereas the tumor volume of the group in which the anti-CTLA-4 antibody was administered in combination with Compound 1 was decreased by a staggering 46% compared to the tumor volume of the control group in which the vehicle was administered. In terms of the tumor volume measured on Day 23 from the cell line inoculation date, a difference in the tumor volume between the control group and the group in which the anti-CTLA-4 antibody was administered in combination with Compound 1 was found to be less than 0.001 of the p-value in the two-way ANOVA analysis and the analysis by using one-way ANOVA and Tukey's multiple comparison test, resulting in a statistically significant decrease in the tumor volume compared to the control group (see FIGS. 18A-18B).

There was no statistically significant difference in weight changes between the drug administration group and the control group in which only the vehicle was administered during the entire study period (see FIG. 19).

Example 5. Anti-Tumor Effect in Bladder Cancer Mouse Model

Example 5.1. Preparation of Bladder Cancer Mouse Models and Study Drugs

C3H/HeN female mice, 7 weeks old, were purchased from OrientBio. $2.5\times10^5$ MBT2 cell lines (Murine bladder cancer cells) were injected subcutaneously into the right flank of each mouse to transplant a cancer cell line. The MBT2 cell line transplantation date was determined as Day 0, and the tumor volume was measured on Day 6. The average tumor volume on Day 6 was found to be 50 $mm^3$, and mice were selected to maintain a constant average and deviation for each group by excluding individuals having a significantly larger tumor volume or a significantly smaller tumor volume than the average tumor size.

A 0.9% physiological saline solution was prepared as a vehicle, and a mixed solution of an anti-PD-1 antibody (BioXCell) and PBS, and a mixed solution of Compound 1 and the vehicle were prepared as study drugs.

Example 5.2. Method for Administration, Measurement Variables, and Statistical Analysis of Study Drugs The mice selected in Example 5.1 were assigned to a control group, a group in which an anti-PD-1 antibody was administered, a group in which Compound 1 was administered, or a group in which Compound 1 was administered in combination with an anti-PD-1 antibody, respectively. Drugs were administered from Day 6 to Day 28 from the MBT2 cell line transplantation date. The dose and administration method of the drug administered to each group are shown in Table 7 below, and when administered orally (p.o) and intraperitoneally (i.p.), the dose was 10 mL/kg in the both cases.

TABLE 7

| Drug | Number of mice |
|---|---|
| Vehicle, twice a day (p.o.) | 12 |
| Compound 1, 15 mg/kg, twice a day (p.o.) | 11 |
| Mouse anti-PD-1 antibody, 12.5 mg/kg, twice a week (i.p.) | 9 |
| Mouse anti-PD-1 antibody, 12.5 mg/kg, twice a week (i.p.) + Compound 1, 50 mg/kg, twice a day (p.o.) | 13 |

The mouse tumor volume and weight were measured three times a week during the study period after the drug administration. The tumor volume was measured by the same method as the method for measuring the tumor volume in Example 1.1.2. Meanwhile, when the tumor volume of individual mice is greater than 1,500 $mm^3$ or is just before the moribund state due to deterioration of health, the mouse was euthanized and the study was terminated, and when the tumor volume was less than ¼ of the tumor volume of the euthanasia criteria, it was classified as a responder to the drug. Survival rates were calculated using the date of death of individual mice or the date of euthanasia in which the tumor volume of individual mice is greater than 1,500 $mm^3$, and the significant difference in survival rates was analyzed by using Kaplan-Meier survival curve (survival curve) analysis (Prism 5.0).

Example 5.3. Survival Rates and Weight Changes

The results of measuring the ratio of responders to the drug based on the tumor volume measured on Day 30 from the cell line inoculation date are shown in Table 8 below.

TABLE 8

| Drug | Response individual ratio |
|---|---|
| Vehicle, twice a day (p.o) | 0/12(0%) |
| Compound 1, 15 mg/kg, twice a day (p.o.) | 1/11(9%) |
| Mouse anti-PD-1 antibody, 12.5 mg/kg, twice a week (i.p.) | 2/9(22%) |
| Mouse anti-PD-1 antibody, 12.5 mg/kg, twice a week (i.p.) + Compound 1, 50 mg/kg, twice a day (p.o.) | 4/13(33%) |

It was confirmed that the group in which the anti-PD-1 antibody was administered in combination with Compound 1 showed a higher rate of responders than the group in which the anti-PD-1 antibody was administered alone, the group in which Compound 1 was administered alone, or the control group in which the vehicle was administered (Table 8, FIGS. 20A-20B), as well as the survival rate was significantly increased compared to the vehicle control group in the Kaplan-Meier survival rate (log-rank test, p-value=0.0042) (see FIGS. 20A-20B).

There was no statistically significant difference in weight changes between the drug administration group and the control group in which only the vehicle was administered during the entire study period (see FIG. 21).

Example 6. Anti-Tumor Effect in Cervical Cancer Animal Model

A 0.9% physiological saline solution was prepared as a vehicle, and a mixed solution of a mouse anti-CTLA-4 antibody and PBS, a mixed solution of a mouse anti-PD-1 antibody and PBS, a mixed solution of the vehicle and lenvatinib, and a mixed solution of Compound 1 and the vehicle were prepared.

Female C57BL/6 mice, 6-8 weeks old, were purchased, and $3\times10^6$ U14 cell lines were subcutaneously injected into the flank of each mouse to transplant a cancer cell line. The U14 cell line transplantation date was determined as Day 0, and the tumor size was measured on Day 7, and mice were classified so that there is no difference between the deviations in the average tumor volume of 50 $mm^3$ on Day 7 for each group. The classified mice were assigned to the groups listed in Table 9 below, and vehicles or drugs were administered, and the drug administration was initiated on Day 7 from the cell line inoculation date, and the study was terminated on Day 27 from the drug administration initiation date, and when administered orally (p.o) and intraperitoneally (i.p.) the administration volume was 5 mL/kg in the both cases.

TABLE 9

| Drug | Number of mice |
|---|---|
| Vehicle, twice a day (p.o.) | 10 |
| Mouse anti-PD-1 antibody, 10 mg/kg, once every three days (i.p.) | 10 |
| Compound 1, 50 mg/kg, twice a day (p.o.) | 10 |
| Mouse anti-CTLA-4 antibody, 3 mg/kg, once every three days (i.p.) | 10 |
| Mouse anti-CTLA-4 antibody, 10 mg/kg, once every three days (i.p.) | 10 |
| Lenvatinib, 10 mg/kg, once a day (p.o.) | 10 |
| Mouse anti-PD-1 antibody, 10 mg/kg, once every three days (i.p.) + Compound 1, 50 mg/kg, twice a day (p.o.) | 10 |
| Mouse anti-CTLA-4 antibody, 3 mg/kg, once every three days (i.p.) + Compound 1, 50 mg/kg, twice a day (p.o.) | 10 |
| Mouse anti-CTLA-4 antibody, 10 mg/kg, once every three days (i.p.) + Compound 1, 50 mg/kg, twice a day (p.o.) | 10 |
| Mouse anti-PD-1 antibody, 10 mg/kg, once every three days (i.p.) + Mouse anti-CTLA-4 antibody, 10 mg/kg, once every three days (i.p.) | 10 |
| Lenvatinib, 10 mg/kg, once a day (p.o.) + Compound 1, 50 mg/kg, twice a day (p.o.) | 10 |
| Mouse anti-CTLA-4 antibody, 3 mg/kg, once every three days (i.p.) + Lenvatinib, 10 mg/kg, twice a day (p.o.) | 10 |
| Mouse anti-PD-1 antibody, 10 mg/kg, once every three days (i.p.) + Lenvatinib, 10 mg/kg, twice a day (p.o.) | 10 |
| Mouse anti-PD-1 antibody, 10 mg/kg, once every three days (i.p.) + Mouse anti-CTLA-4 antibody, 3 mg/kg, once every three days (i.p.) + Compound 1, 50 mg/kg, twice a day (p.o.) | 10 |
| Mouse anti-PD-1 antibody, 10 mg/kg, once every three days (i.p.) + Mouse anti-CTLA-4 antibody, 10 mg/kg, once every three days (i.p.) + Compound 1, 50 mg/kg, twice a day (p.o.) | 10 |
| Lenvatinib, 10 mg/kg, once a day (p.o.) + Mouse anti-CTLA-4 antibody, 3 mg/kg, once every three days (i.p.) + Compound 1, 50 mg/kg, twice a day (p.o.) | 10 |
| Lenvatinib, 10 mg/kg, once a day (p.o.) + Mouse anti-PD-1 antibody, 10 mg/kg, once every three days (i.p.) + Compound 1, 50 mg/kg, twice a day (p.o.) | 10 |

The mouse tumor volume and weight were measured twice a week during the study period after the drug administration. In this case, the mouse tumor volume was calculated by the same method as the tumor volume calculation method of Example 1.1.2. Meanwhile, when the tumor volume of an individual mouse was greater than 3,000 mm$^3$, the corresponding mouse was euthanized and the study was terminated.

Example 7. Anti-Tumor Effect in Head and Neck Squamous Cell Carcinoma Animal Model A 0.9% physiological saline solution was prepared as a vehicle, and a mixed solution of a mouse anti-CTLA-4 antibody and PBS, a mixed solution of a mouse anti-PD-1 antibody and PBS, a mixed solution of the vehicle and lenvatinib, and a mixed solution of Compound 1 and the vehicle were prepared.

Female C57BL/6 mice, 6-8 weeks old, were purchased, and 3×10$^6$ MOC1 cell lines were subcutaneously injected into the flank of each mouse to transplant a cancer cell line. The MOC1 cell line transplantation date was determined as Day 0, and the tumor size was measured on Day 7, and mice were classified so that there is no difference between the deviations in the average tumor volume of 50 mm$^3$ on Day 7 for each group. The classified mice were assigned to the groups listed in Table 10 below, and vehicles or drugs were administered, and the drug administration was initiated on Day 7 from the cell line inoculation date, and the study was terminated on Day 27 from the drug administration initiation date, and when administered orally (p.o) and intraperitoneally (i.p.) the administration volume was 5 mL/kg in the both cases.

TABLE 10

| Drug | Number of mice |
|---|---|
| Vehicle, twice a day (p.o.) | 10 |
| Mouse anti-PD-1 antibody, 10 mg/kg, once every three days (i.p.) | 10 |
| Compound 1, 50 mg/kg, twice a day (p.o.) | 10 |
| Mouse anti-CTLA-4 antibody, 3 mg/kg, once every three days (i.p.) | 10 |
| Mouse anti-CTLA-4 antibody, 10 mg/kg, once every three days (i.p.) | 10 |
| Lenvatinib, 10 mg/kg, once a day (p.o.) | 10 |
| Mouse anti-PD-1 antibody, 10 mg/kg, once every three days (i.p.) + Compound 1, 50 mg/kg, twice a day (p.o.) | 10 |

TABLE 10-continued

| Drug | Number of mice |
|---|---|
| Mouse anti-CTLA-4 antibody, 3 mg/kg, once every three days (i.p.) + Compound 1, 50 mg/kg, twice a day (p.o.) | 10 |
| Mouse anti-CTLA-4 antibody, 10 mg/kg, once every three days (i.p.) + Compound 1, 50 mg/kg, twice a day (p.o.) | 10 |
| Mouse anti-PD-1 antibody, 10 mg/kg, once every three days (i.p.) + Mouse anti-CTLA-4 antibody, 10 mg/kg, once every three days (i.p.) | 10 |
| Lenvatinib, 10 mg/kg, once a day (p.o.) + Compound 1, 50 mg/kg, twice a day (p.o.) | 10 |
| Mouse anti-CTLA-4 antibody, 3 mg/kg, once every three days (i.p.) + Lenvatinib, 10 mg/kg, twice a day (p.o.) | 10 |
| Mouse anti-PD-1 antibody, 10 mg/kg, once every three days (i.p.) + Lenvatinib, 10 mg/kg, twice a day (p.o.) | 10 |
| Mouse anti-PD-1 antibody, 10 mg/kg, once every three days (i.p.) + Mouse anti-CTLA-4 antibody, 3 mg/kg, once every three days (i.p.) + Compound 1, 50 mg/kg, twice a day (p.o.) | 10 |
| Mouse anti-PD-1 antibody, 10 mg/kg, once every three days (i.p.) + Mouse anti-CTLA-4 antibody, 10 mg/kg, once every three days (i.p.) + Compound 1, 50 mg/kg, twice a day (p.o.) | 10 |
| Lenvatinib, 10 mg/kg, once a day (p.o.) + Mouse anti-CTLA-4 antibody, 3 mg/kg, once every three days (i.p.) + Compound 1, 50 mg/kg, twice a day (p.o.) | 10 |
| Lenvatinib, 10 mg/kg, once a day (p.o.) + Mouse anti-PD-1 antibody, 10 mg/kg, once every three days (i.p.) + Compound 1, 50 mg/kg, twice a day (p.o.) | 10 |

The mouse tumor volume and weight were measured twice a week during the study period after the drug administration. In this case, the mouse tumor volume was calculated by the same method as the tumor volume calculation method of Example 1.1.2. Meanwhile, when the tumor volume of an individual mouse was greater than 3,000 $mm^3$, the corresponding mouse was euthanized and the study was terminated.

Example 8. Anti-Tumor Effect in Liver Cancer Animal Model

A 0.9% physiological saline solution was prepared as a vehicle, and a mixed solution of a mouse anti-CTLA-4 antibody and PBS, a mixed solution of a mouse anti-PD-1 antibody and PBS, a mixed solution of the vehicle and lenvatinib, and a mixed solution of Compound 1 and the vehicle were prepared.

Female BALB/6 mice, 6-8 weeks old, were purchased, and $1\times10^6$ H22 cell lines (Murine liver cancer cell line) were subcutaneously injected into the flank of each mouse to transplant a cancer cell line. The H22 cell line transplantation date was determined as Day 0, and the tumor size was measured on Day 7, and mice were classified so that there is no difference between the deviations in the average tumor volume of 50 $mm^3$ on Day 7 for each group. The classified mice were assigned to the groups listed in Table 11 below, and vehicles or drugs were administered, and the drug administration was initiated on Day 7 from the cell line inoculation date, and the study was terminated on Day 27 from the drug administration initiation date, and when administered orally (p.o) and intraperitoneally (i.p.) the administration volume was 5 mL/kg in the both cases.

TABLE 11

| Drug | Number of mice |
|---|---|
| Vehicle, twice a day (p.o.) | 10 |
| Mouse anti-PD-1 antibody, 10 mg/kg, once every three days (i.p.) | 10 |
| Compound 1, 50 mg/kg, twice a day (p.o.) | 10 |
| Mouse anti-CTLA-4 antibody, 3 mg/kg, once every three days (i.p.) | 10 |
| Mouse anti-CTLA-4 antibody, 10 mg/kg, once every three days (i.p.) | 10 |
| Lenvatinib, 10 mg/kg, once a day (p.o.) | 10 |
| Mouse anti-PD-1 antibody, 10 mg/kg, once every three days (i.p.) + Compound 1, 50 mg/kg, twice a day (p.o.) | 10 |
| Mouse anti-CTLA-4 antibody, 3 mg/kg, once every three days (i.p.) + Compound 1, 50 mg/kg, twice a day (p.o.) | 10 |
| Mouse anti-CTLA-4 antibody, 10 mg/kg, once every three days (i.p.) + Compound 1, 50 mg/kg, twice a day (p.o.) | 10 |
| Mouse anti-PD-1 antibody, 10 mg/kg, once every three days (i.p.) + Mouse anti-CTLA-4 antibody, 10 mg/kg, once every three days (i.p.) | 10 |
| Lenvatinib, 10 mg/kg, once a day (p.o.) + Compound 1, 50 mg/kg, twice a day (p.o.) | 10 |
| Mouse anti-CTLA-4 antibody, 3 mg/kg, once every three days (i.p.) + Lenvatinib, 10 mg/kg, twice a day (p.o.) | 10 |
| Mouse anti-PD-1 antibody, 10 mg/kg, once every three days (i.p.) + Lenvatinib, 10 mg/kg, twice a day (p.o.) | 10 |

TABLE 11-continued

| Drug | Number of mice |
|---|---|
| Mouse anti-PD-1 antibody, 10 mg/kg, once every three days (i.p.) + Mouse anti-CTLA-4 antibody, 3 mg/kg, once every three days (i.p.) + Compound 1, 50 mg/kg, twice a day (p.o.) | 10 |
| Mouse anti-PD-1 antibody, 10 mg/kg, once every three days (i.p.) + Mouse anti-CTLA-4 antibody, 10 mg/kg, once every three days (i.p.) + Compound 1, 50 mg/kg, twice a day (p.o.) | 10 |
| Lenvatinib, 10 mg/kg, once a day (p.o.) + Mouse anti-CTLA-4 antibody, 3 mg/kg, once every three days (i.p.) + Compound 1, 50 mg/kg, twice a day (p.o.) | 10 |
| Lenvatinib, 10 mg/kg, once a day (p.o.) + Mouse anti-PD-1 antibody, 10 mg/kg, once every three days (i.p.) + Compound 1, 50 mg/kg, twice a day (p.o.) | 10 |

The mouse tumor volume and weight were measured twice a week during the study period after the drug administration. In this case, the mouse tumor volume was calculated by the same method as the tumor volume calculation method of Example 1.1.2. Meanwhile, when the tumor volume of an individual mouse was greater than 3,000 $mm^3$, the corresponding mouse was euthanized and the study was terminated.

The invention claimed is:

1. A method for preventing or treating a tumor in a subject in need thereof, the method comprising administering to the subject:

(a) a low-molecular kinase inhibitor that blocks the signaling pathway of Transforming growth factor-β (TGF-β); and (b) an immune checkpoint regulator, a receptor tyrosine kinase inhibitor, or a combination thereof, wherein the immune checkpoint regulator of (b) is anti-PD-1 antibody, anti-PD-L1 antibody or anti-CTLA-4 antibody, and the receptor tyrosine kinase inhibitor of (b) is lenvatinib; and wherein the low molecular kinase inhibitor of (a) is a compound selected from the group consisting of:

1) 1-[6-(6-methyl-pyridin-2-yl)-5-quinoxalin-6-yl-2,3-dihydro-imidazo[1,2-a]imidazol-1-yl]-ethanone;
2) 6-[2-(6-methyl-pyridin-2-yl)-6,7-dihydro-5H-imidazo[1,2-a]imidazol-3-yl]-quinoxaline;
3) 6-[2-(6-methyl-pyridin-2-yl)-5,6,7,8-tetrahydro-imidazo[1,2-a]pyrimidin-3-yl]-quinoxaline;
4) 6-[2-(6-methyl-pyridin-2-yl)-6,7-dihydro-5H-imidazo[1,2-a]imidazol-3-yl]-quinoline;
5) 6-[2-(6-methyl-pyridin-2-yl)-5,6,7,8-tetrahydro-imidazo[1,2-a]pyrimidin-3-yl]-quinoline;
6) 2-[2-(6-methyl-pyridin-2-yl)-6,7-dihydro-5H-imidazo[1,2-a]imidazol-3-yl]-thieno[3,2-c]pyridine;
7) 6-[2-(6-methyl-pyridin-2-yl)-6,7-dihydro-5H-imidazo[1,2-a]imidazol-3-yl]-benzothiazole;
8) 5-benzo[b]thiophen-5-yl-6-(6-methyl-pyridin-2-yl)-2,3-dihydro-1H-imidazo[1,2-a]imidazole;
9) 6-(6-(6-methylpyridin-2-yl)-2,3-dihydro-1H-imidazo[1,2-a]imidazol-5-yl)-[1,2,4]triazole[1,5-a]pyridine;
10) 5-[2-(6-methyl-pyridin-2-yl)-6,7-dihydro-5H-imidazo[1,2-a]imidazol-3-yl]-benzoxazole;
11) 4-[2-(6-methyl-pyridin-2-yl)-6,7-dihydro-5H-imidazo[1,2-a]imidazol-3-yl]-quinoline;
12) 5-benzo[1,3]dioxol-5-yl-6-(6-methyl-pyridin-2-yl)-2,3-dihydro-1H-imidazo[1,2-a]imidazole;
13) 5-(2,3-dihydro-benzo[1,4]dioxin-6-yl)-6-(6-methyl-pyridin-2-yl)-2,3-dihydro-1H-imidazo[1,2-a]imidazole;
14) 7-[2-(6-methyl-pyridin-2-yl)-6,7-dihydro-5H-imidazo[1,2-a]imidazol-3-yl]-2-pyrazol-1-yl-quinoxaline;
15) dimethyl-(2-{7-[2-(6-methyl-pyridin-2-yl)-6,7-dihydro-5H-imidazo[1,2-a]imidazol-3-yl]-quinoxalin-2-yloxy}-ethyl)-amine;
16) 2-methoxy-7-[2-(6-methyl-pyridin-2-yl)-6,7-dihydro-5H-imidazo[1,2-a]imidazol-3-yl]-quinoxaline;
17) 5-(3,5-dimethoxyphenyl)-6-(6-methylpyridin-2-yl)-2,3-dihydro-1H-imidazo[1,2-a]imidazole;
18) N,N-dimethyl-4-(6-(6-methylpyridin-2-yl)-2,3-dihydro-1H-imidazo[1,2-a]imidazol-5-yl)aniline;
19) 4-(6-(6-methylpyridin-2-yl)-2,3-dihydro-1H-imidazo[1,2-a]imidazol-5-yl)benzonitrile;
20) 2-methyl-6-(6-(6-methylpyridin-2-yl)-2,3-dihydro-1H-imidazo[1,2-a]imidazol-5-yl)quinoline;
21) 4-(6-(6-methylpyridin-2-yl)-2,3-dihydro-1H-imidazo[1,2-a]imidazol-5-yl)aniline;
22) N-(4-(6-(6-methylpyridin-2-yl)-2,3-dihydro-1H-imidazo[1,2-a]imidazol-5-yl)phenyl)acetamide;
23) N-(4-(6-(6-methylpyridin-2-yl)-2,3-dihydro-1H-imidazo[1,2-a]imidazol-5-yl)phenyl)methanesulfonamide;
24) tert-butyl (4-(6-(6-methylpyridin-2-yl)-2,3-dihydro-1H-imidazo[1,2-a]imidazol-5-yl)phenyl)carbamate;
25) 5-(4-(4-methylpiperazin-1-yl)phenyl)-6-(6-methylpyridin-2-yl)-2,3-dihydro-1H-imidazo[1,2-a]imidazole;
26) 4-(4-(6-(6-methylpyridin-2-yl)-2,3-dihydro-1H-imidazo[1,2-a]imidazol-5-yl)phenyl)morpholine;
27) 6-(6-methylpyridin-2-yl)-5-(m-tolyl)-2,3-dihydro-1H-imidazo[1,2-a]imidazole;
28) 5-(4-methoxyphenyl)-6-(6-methylpyridin-2-yl)-2,3-dihydro-1H-imidazo[1,2-a]imidazole;
29) 6-(6-methylpyridin-2-yl)-5-(4-(trifluoromethyl)phenyl)-2,3-dihydro-1H-imidazo[1,2-a]imidazole;
30) 6-(6-methylpyridin-2-yl)-5-(4-(methylthio)phenyl)-2,3-dihydro-1H-imidazo[1,2-a]imidazole;
31) 5-(3-fluoro-4-methoxyphenyl)-6-(6-methylpyridin-2-yl)-2,3-dihydro-1H-imidazo[1,2-a]imidazole;
32) 5-(4-fluorophenyl)-6-(6-methylpyridin-2-yl)-2,3-dihydro-1H-imidazo[1,2-a]imidazole;
33) 1-acetyl-6-(6-methyl-pyridin-2-yl)-5-thieno[3,2-c]pyridin-2-yl-2,3-dihydro-1H-imidazo[1,2-a]imidazol-2-carboxylic acid ethyl ester;
34) 6-(6-methyl-pyridin-2-yl)-5-thieno[3,2-c]pyridin-2-yl-2,3-dihydro-1H-imidazo[1,2-a]imidazol-2-carboxylic acid ethyl ester;
35) [6-(6-methyl-pyridin-2-yl)-5-thieno[3,2-c]pyridin-2-yl-2,3-dihydro-1H-imidazo[1,2-a]imidazol-2-yl]-methanol;

36) 1-acetyl-6-(6-methyl-pyridin-2-yl)-5-thieno[3,2-c]pyridin-2-yl-2,3-dihydro-1H-imidazo[1,2-a]imidazole-2-carbonitrile;

37) 6-(6-methyl-pyridin-2-yl)-5-thieno[3,2-c]pyridin-2-yl-2,3-dihydro-1H-imidazo[1,2-a]imidazole-2-carbonitrile;

38) 6-(6-methyl-pyridin-2-yl)-5-thieno[3,2-c]pyridin-2-yl-2,3-dihydro-1H-imidazo[1,2-a]imidazol-2-carboxylic acid amide;

39) (6-(6-methylpyridin-2-yl)-5-(thieno[3,2-c]pyridin-2-yl)-2,3-dihydro-1H-imidazo[1,2-a]imidazol-2-yl)methanamine; and 40) N-((6-(6-methylpyridin-2-yl)-5-(thieno[3,2-c]pyridin-2-yl)-2,3-dihydro-1H-imidazo[1,2-a]imidazol-2-yl)methyl)acetamide, or a pharmaceutically acceptable salt thereof.

2. The method of claim 1, wherein the tumor is selected from the group consisting of melanoma, sarcoma, brain tumor, breast cancer, adrenal cancer, thyroid cancer, pancreatic cancer, pituitary carcinoma, glioblastoma, ocular cancer, vaginal cancer, vulvar cancer, cervical cancer, endometrial carcinoma, uterine cancer, ovarian cancer, esophageal cancer, stomach cancer, colon cancer, rectal cancer, liver cancer, gallbladder cancer, cholangiocarcinoma, lung cancer, testicular cancer, prostate cancer, penile cancer, oral cancer, basal cancer, salivary gland cancer, pharynx cancer, skin cancer, kidney cancer, Wilms' tumor, bladder cancer, head and neck cancer, head and neck squamous cell carcinoma, hepatocellular carcinoma, appendix cancer, bronchial cancer, chorial carcinoma, chordoma, ependymoma, gastrointestinal stromal tumor (GIST), neuroendocrine cancer, and urethral cancer.

3. The method of claim 1, wherein the tumor is a solid tumor.

4. The method of claim 1, wherein the (a) low-molecular kinase inhibitor that blocks the signaling pathway of TGF-β and the (b) immune checkpoint regulator, receptor tyrosine kinase inhibitor, or combination thereof are administered by a route selected from the group consisting of topical administration, parenteral administration, oral administration, intravenous administration, intramuscular administration, subcutaneous administration, or a combination thereof.

5. The method of claim 1, wherein the (a) low-molecular kinase inhibitor that blocks the signaling pathway of TGF-β; and/or the (b) immune checkpoint regulator, receptor tyrosine kinase inhibitor, or combination thereof, are formulated as separate dosage forms or a single dosage form.

6. The method of claim 1, wherein the (a) low-molecular kinase inhibitor that blocks the signaling pathway of TGF-β and the (b) immune checkpoint regulator, receptor tyrosine kinase inhibitor, or combination thereof are administered simultaneously, sequentially, or separately.

* * * * *